(12) United States Patent
Hagmann et al.

(10) Patent No.: US 7,514,409 B2
(45) Date of Patent: Apr. 7, 2009

(54) VLA-4 ANTAGONISTS

(75) Inventors: William K. Hagmann, Westfield, NJ (US); Linus S. Lin, Westfield, NJ (US); Ping Liu, Westfield, NJ (US); Richard A. Mumford, Red Bank, NJ (US); Thomas S. Reger, San Diego, CA (US); Nicholas D. Smith, San Diego, CA (US); Nicholas S. Stock, San Diego, CA (US); Jasmine Zunic, San Diego, CA (US)

(73) Assignee: Merck & Co., Inc., Rahway, NJ (US)

( * ) Notice: Subject to any disclaimer, the term of this patent is extended or adjusted under 35 U.S.C. 154(b) by 215 days.

(21) Appl. No.: 10/591,820

(22) PCT Filed: Mar. 7, 2005

(86) PCT No.: PCT/US2005/007252

§ 371 (c)(1),
(2), (4) Date: Sep. 7, 2006

(87) PCT Pub. No.: WO2005/087760

PCT Pub. Date: Sep. 22, 2005

(65) Prior Publication Data

US 2007/0179190 A1    Aug. 2, 2007

Related U.S. Application Data

(60) Provisional application No. 60/615,477, filed on Oct. 1, 2004, provisional application No. 60/552,057, filed on Mar. 10, 2004.

(51) Int. Cl.
*A61K 38/05* (2006.01)
(52) U.S. Cl. ......................................................... 514/19
(58) Field of Classification Search .................. None
See application file for complete search history.

(56) References Cited

U.S. PATENT DOCUMENTS

| | | | | |
|---|---|---|---|---|
| 6,229,011 B1 * | 5/2001 | Chen et al. | ................... | 544/171 |
| 6,288,267 B1 * | 9/2001 | Hull et al. | ................... | 560/149 |
| 6,291,511 B1 * | 9/2001 | Durette et al. | ............... | 514/423 |
| 6,388,084 B1 * | 5/2002 | Kaplan et al. | ............... | 546/291 |
| 6,559,174 B2 * | 5/2003 | Lin et al. | ..................... | 514/406 |
| 6,583,139 B1 | 6/2003 | Thorsett et al. | | |
| 6,806,365 B2 * | 10/2004 | Chen et al. | ................... | 544/169 |
| 6,855,706 B2 * | 2/2005 | Tanaka et al. | .......... | 514/210.17 |
| 6,855,708 B2 * | 2/2005 | Lin et al. | ................ | 514/217.01 |
| 6,903,075 B1 * | 6/2005 | Durette et al. | ................ | 514/19 |
| 6,943,180 B2 * | 9/2005 | Doherty et al. | ............. | 514/335 |
| 7,008,949 B2 * | 3/2006 | Konradi et al. | .............. | 514/275 |

FOREIGN PATENT DOCUMENTS

WO    WO 02/074761 A1    9/2002

OTHER PUBLICATIONS

Lin et al., "Very late antigen 4 (VLA4) antagonists as anti-inflammatory agents," Curr. Op. Chem. Biol., 1998, 2, 453-7.*
Yang et al., "VLA-4 Antagonists: Potent Inhibitors of Lymphocyte Migration," Med. Res. Rev., 2003, 23, 369-392.*
Lobb et al., "Small molecule antagonists of alpha4 integrins: novel drugs for asthma," Exp. Op. Investigational Drugs, 1999, 8, 935-45.*
Tilley, "VLA-4 antagonists," Exp. Op. Ther. Patents, 2002, 12, 991-1008.*
George A. Doherty, et al., *Bioorganic & Medicinal Chemistry Letters*, vol. 13 (17), pp. 2937-2938 (2003).

* cited by examiner

*Primary Examiner*—Cecilia Tsang
*Assistant Examiner*—Christina Marchetti Bradley
(74) *Attorney, Agent, or Firm*—Mollie M. Yang; Valerie J. Camara

(57) ABSTRACT

Compounds of Formula I are antagonists of VLA-4, and as such are useful in the inhibition or prevention of cell adhesion and cell-adhesion mediated pathologies. These compounds may be formulated into pharmaceutical compositions and are suitable for use in the treatment of inflammatory bowel disease including ulcerative colitis and Crohn's disease, multiple sclerosis, asthma, and rheumatoid arthritis.

9 Claims, No Drawings

VLA-4 ANTAGONISTS

CROSS REFERENCE TO RELATED APPLICATIONS

This application is the National Stage of International Application No. PCT/US2005/007252, filed 07 Mar. 2005 which claims the benefit under 35 U.S.C. 119(e) of U.S. Provisional Application No. 60/552,057 filed 10 Mar. 2004 and U.S. Provisional Application No. 60/615,477 filed 01 Oct. 2004.

SUMMARY OF THE INVENTION

Substituted N-[N-(cyanophenyl)sulfonyl-prolyl]-phenylalanine derivatives of the present invention are antagonists of the VLA-4 integrin and are useful in the treatment, prevention and suppression of diseases mediated by VLA-4-binding and cell adhesion and activation. Moreover, the compounds of the present invention demonstrate significant receptor occupancy of VLA-4 bearing cells after oral administration and are suitable for once-, twice-, or thrice-a-day oral administration. This invention also relates to compositions containing such compounds and methods of treatment using such compounds.

BACKGROUND OF THE INVENTION

VLA-4 ("very late antigen-4"; CD49d/CD29; or $\alpha_4\beta_1$) is an integrin expressed on all leukocytes, except platelets and mature neutrophils, including dendritic cells and macrophage-like cells and is a key mediator of the cell-cell and cell-matrix interactions of these cell types. The ligands for VLA-4 include vascular cell adhesion molecule-1 (VCAM-1), the CS-1 domain of fibronectin (FN), and the matrix protein, osteopontin. Neutralizing anti-$\alpha_4$ antibodies or blocking peptides that inhibit the interaction between VLA-4 and its ligands have been shown to be efficacious both prophylactically and therapeutically in several animal models of disease including asthma, multiple sclerosis, inflammatory bowel disease, and rheumatoid arthritis.

The humanized monoclonal antibody against $\alpha_4$, natalizumab (Antegren®, Elan/Biogen), has demonstrated efficacy in the treatment of multiple sclerosis (D. H. Miller et al., *New England Journal of Medicine*, 348, 15 (2003)) and Crohn's disease (S. Ghosh et al. *New England Journal of Medicine*, 348, 23 (2003)). There are also several VLA-4 antagonists in early clinical trials for treatment of asthma, arthritis, multiple sclerosis, and Crohn's disease.

In the early clinical trials with natalizumab, lymphocytosis (a surrogate marker for blockade of VLA-4 function) and >80% receptor occupancy were observed. A small molecule VLA-4 antagonist was reported to demonstrate functional activity in the rat experimental autoimmune encephalomyelitis (EAE) assay, an animal model of multiple sclerosis following subcutaneous administration (D. R. Leone et al., *J. Pharmacol. Exper. Therap.*, 305, 1150 (2003). This compound was shown to induce lymphocytosis, and to have a slow dissociation rate (off-rate) resulting in significant and sustained receptor occupancy on VLA-4-bearing cells. There was a positive correlation between receptor occupancy, lymphocytosis, and efficacy in the EAE model described in this manuscript.

A series of isonicotinoyl-L-aminophenylalanine derivatives shown to possess slow dissociation (off-rate) from VLA-4 on Jurkat cells were reported in G. Doherty et al., *Bioorganic & Medicinal Chemistry Letters*, 13, 1891 (2003). However, the compound that was further characterized demonstrated very poor pharmacokinetic properties such as low oral bioavailability, moderate to high plasma clearance and a short half-life rendering it unsuitable for oral administration. Compounds of the present invention are potent antagonists of VLA-4 capable of achieving and maintaining receptor occupancy for a time sufficient to allow for oral administration.

DETAILED DESCRIPTION OF THE INVENTION

The present invention provides compounds of Formula I:

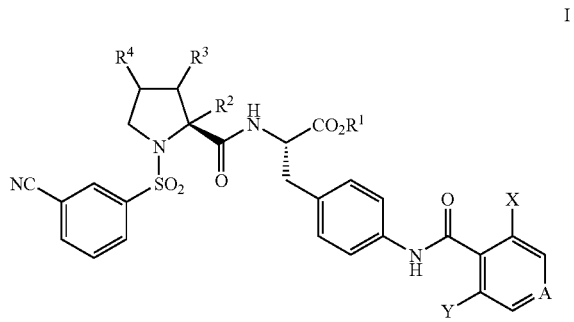

I or a pharmaceutically acceptable salt thereof, wherein:

A is N or $N^+$—$O^-$;

X and Y are independently selected from halogen, $C_{1-3}$alkyl, and $C_{1-3}$alkoxy;

$R^1$ is selected from (1) hydrogen, (2) $C_{1-10}$alkyl, (3) —($C_{1-10}$alkyl)-aryl, (4) —($C_{1-10}$alkyl)-O—$C_{1-10}$alkyl, (5) —($C_{1-10}$alkyl)-OC(O)—$C_{1-10}$alkyl, (6) —($C_{1-10}$alkyl)-OC(O)-aryl, (7) —($C_{1-10}$alkyl)-OC(O)O—$C_{1-10}$alkyl and (8) —($C_{1-10}$alkyl)$N^+$($C_{1-3}$alkyl)$_3$; wherein alkyl is optionally substituted with one to three substituents independently selected from $R^a$, and aryl is optionally substituted with one to three substituents independently selected from $R^b$;

$R^2$ is hydrogen or methyl;

$R^3$ and $R^4$ are independently selected from (1) hydrogen, (2) —$NR^dR^e$, (3) —$NR^dS(O)_mR^e$, (4) —$NR^dC(O)R^e$, (5) —$NR^dC(O)OR^e$, and (6) —$NR^dC(O)NR^dR^e$, with the proviso that $R^3$ and $R^4$ are not both hydrogen;

$R^a$ is selected from (1) —$OR^d$, (2) —$NR^dS(O)_mR^e$, (3) —$NO_2$, (4) halogen, (5) —$S(O)_mR^d$, (6) —$SR^d$, (7) —$S(O)_2OR^d$, (8) —$S(O)_mNR^dR^e$, (9) —$NR^dR^e$, (10) —$O(CR^fR^g)_nNR^dR^e$, (11) —$C(O)R^d$, (12) —$CO_2R^d$, (13) —$CO_2(CR^fR^g)_nCONR^dR^e$, (14) —$OC(O)R^d$, (15) —$CN$, (16) —$C(O)NR^dR^e$, (17) —$NR^dC(O)R^e$, (18) —$OC(O)NR^dR^e$, (19) —$NR^dC(O)OR^e$, (20) —$NR^dC(O)NR^dR^e$, (21) —$CR^d(N$—$OR^e)$, (22) $CF_3$, (23) —$OCF_3$, (24) $C_{3-8}$cycloalkyl, and (25) heterocyclyl; wherein cycloalkyl and heterocyclyl are optionally substituted with one to three groups independently selected from $R^c$;

$R^b$ is selected from (1) a group selected from $R^a$, (2) C1-10 alkyl, (3) $C_{2-10}$ alkenyl (4) $C_{2-10}$ alkynyl, (5) aryl, and (6) —($C_{1-10}$alkyl)-aryl, wherein alkyl, alkenyl, alkynyl, and aryl are optionally substituted with one to three substituents selected from a group independently selected from $R^c$;

$R^c$ is (1) halogen, (2) amino, (3) carboxy, (4) $C_{1-4}$alkyl, (5) $C_{1-4}$alkoxy, (6) aryl, (7) —($C_{1-4}$alkyl)-aryl, (8) hydroxy, (9) $CF_3$, (10) $OC(O)C_{1-4}$alkyl, (11) $OC(O)NR^fR^g$, or (12) aryloxy;

$R^d$ and $R^e$ are independently selected from hydrogen, $C_{1-10}$alkyl, $C_{2-10}$alkenyl, $C_{2-10}$alkynyl, Cy and —($C_{1-10}$alkyl)-Cy, wherein alkyl, alkenyl, alkynyl and Cy are optionally substituted with one to four substituents independently selected from $R^c$; or $R^d$ and $R^e$ together with the atom(s) to which they are attached form a heterocyclic ring of 4 to 7 members containing 0-2 additional heteroatoms independently selected from O, S and N—$R^h$, and wherein said heterocyclic ring is optionally fused with a $C_{3-8}$ carbocyclic ring or is optional substituted with 1 to 4 groups independently selected from $C_{1-10}$alkyl;

$R^f$ and $R^g$ are independently selected from hydrogen, $C_{1-10}$alkyl, Cy and —($C_{1-10}$alkyl)-Cy; or $R^f$ and $R^g$ together with the carbon to which they are attached form a ring of 5 to 7 members containing 0-2 heteroatoms independently selected from oxygen, sulfur and nitrogen;

$R^h$ is selected from $R^f$ and —C(O)$R^f$;

Cy is selected from cycloalkyl, heterocyclyl, aryl, and heteroaryl; and m is 1 or 2.

In one embodiment of formula I, one of X and Y is halogen and the other is selected from halogen, $C_{1-3}$alkyl and $C_{1-3}$alkoxy. In one subset of this embodiment, one of X and Y is chloro and the other is chloro or methoxy. In another subset X and Y are each chloro.

In another embodiment of formula I, $R^1$ is hydrogen, $C_{1-4}$alkyl, —($C_{1-4}$alkyl)OC(O)—$C_{1-4}$alkyl, or —($C_{1-4}$alkyl)OC(O)—$C_{1-4}$alkyl. In one subset $R^1$ is hydrogen, and in another subset $R^1$ is $C_{1-4}$alkyl.

In another embodiment of formula I, $R^3$ is hydrogen, and $R^4$ is $NR^dR^e$. In one subset of this embodiment, $R^d$ is hydrogen. In a second subset of this embodiment, $R^d$ is hydrogen and $R^e$ is selected from $C_{1-10}$alkyl and cycloalkyl. In a third subset $R^d$ and $R^e$ together with the atom to which they are attached form a heterocyclic ring of 4 to 7 members containing no additional heteroatom and optionally substituted with 1 or 2 groups independently selected from $C_{1-4}$alkyl. Examples of $R^4$ include 1-azetidinyl, 1-pyrrolidinyl, 1-piperidinyl, 2-methyl-1-piperidinyl, 3-methyl-1-piperidinyl, 4-methyl-1-piperidinyl, 3,5-dimethyl-1-piperidinyl, 3,3-dimethyl-1-piperidinyl, 4,4-dimethyl-1-piperidinyl, octahydroquinolin-1-yl, 2-azabicyclo[2.2.2]oct-2-yl, tert-butylamino and cyclobutylamino.

In another embodiment of formula I, $R^3$ is $NR^dR^e$ and $R^4$ is hydrogen. In one subset of this embodiment, $R^d$ is hydrogen. In one subset of this embodiment, a second subset of this embodiment, $R^d$ is hydrogen and $R^e$ is selected from $C_{1-10}$alkyl and cycloalkyl. Examples of $R^3$ include tert-butylamino and cyclobutylamino.

One embodiment of formula I provides compounds of formula Ia:

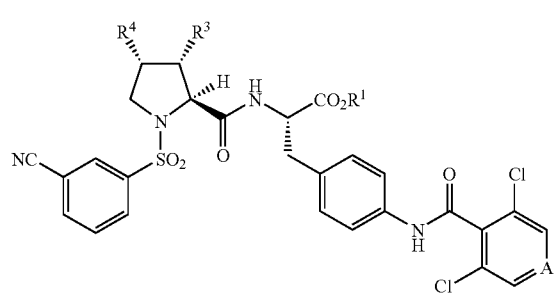

Ia or a pharmaceutically acceptable salt thereof, wherein A is N or $N^+O^-$;

$R^1$ is selected from hydrogen, $C_{1-10}$alkyl, —($C_{1-4}$alkyl)-aryl, —($C_{1-4}$alkyl)-O—$C_{1-4}$alkyl, and —($C_{1-4}$alkyl)-OC(O)—$C_{1-4}$alkyl;

one of $R^3$ and $R^4$ is $NR^dR^e$ and the other is hydrogen.

In one embodiment of formula Ia are compounds wherein $R^d$ is hydrogen and $R^e$ is t-butyl or cyclobutyl or wherein $R^d$, $R^e$ together with the nitrogen atom to which they are attached form a heterocyclic ring with no additional heteroatom and optionally substituted with 1 or 2 groups independently selected from $C_{1-4}$alkyl.

In another embodiment of formula Ia are compounds wherein $R^3$ is hydrogen, $R^4$ is piperidin-1-yl optionally substituted with 1 or 2 groups independently selected from $C_{1-4}$alkyl, and $R^1$ is hydrogen or $C_{1-4}$alkyl Representative compounds of formula I include, but are not limited to:

N-{N-[(3-Cyanobenzene)sulfonyl]-4(R)-cyclobutylamino-(L)-prolyl}-4-[(3',5'-dichloroisonicotinoyl)-amino]-(L)-phenylalanine and ethyl ester thereof;

N-{N-[(3-Cyanobenzene)sulfonyl]-3(S)-tert-butylamino-(L)-prolyl}-4-[(3',5'-dichloroisonicotinoyl)-amino]-(L)-phenylalanine and ethyl, pivaloyloxymethyl, and 1-(ethoxycarbonyloxy)ethyl esters thereof;

N-{N-[(3-Cyanobenzene)sulfonyl]-4(R)-azetidinyl-(L)-prolyl}-4-[(3',5'-dichloroisonicotinoyl)amino]-(L)-phenylalanine, ethyl ester (4R)-1-[(3-cyanophenyl)sulfonyl]-4-(piperidin-1-yl)-L-prolyl-4-[(3,5-dichloroisonicotinoyl)amino]-L-phenylalanine and ethyl ester thereof;

(4R)-1-[(3-cyanophenyl)sulfonyl]-4-(2-methylpiperidin-1-yl)-L-prolyl-4-[(3,5-dichloroisonicotinoyl)-amino]-L-phenylalanine and ethyl ester thereof;

(4R)-1-[(3-cyanophenyl)sulfonyl]-4-(3-methylpiperidin-1-yl)-L-prolyl-4-[(3,5-dichloroisonicotinoyl)-amino]-L-phenylalanine and ethyl ester thereof;

(4R)-1-[(3-cyanophenyl)sulfonyl]-4-(4-methylpiperidin-1-yl)-L-prolyl-4-[(3,5-dichloroisonicotinoyl)-amino]-L-phenylalanine and ethyl ester thereof;

(4R)-1-[(3-cyanophenyl)sulfonyl]-4-(3,5-dimethylpiperidin-1-yl)-L-prolyl-4-[(3,5-dichloroisonicotinoyl)-amino]-L-phenylalanine and ethyl ester thereof;

(4R)-1-[(3-cyanophenyl)sulfonyl]-4-(3,3-dimethylpiperidin-1-yl)-L-prolyl-4-[(3,5-dichloroisonicotinoyl)-amino]-L-phenylalanine and ethyl ester thereof;

(4R)-1-[(3-cyanophenyl)sulfonyl]-4-(4,4-dimethylpiperidin-1-yl)-L-prolyl-4-[(3,5-dichloroisonicotinoyl)-amino]-L-phenylalanine and ethyl ester thereof;

(4R)-1-[(3-cyanophenyl)sulfonyl]-4-(octahydroquinolin-1(2H)-yl)-L-prolyl-4-[(3,5-dichloroisonicotinoyl)amino]-L-phenylalanine and ethyl ester thereof;

(4R)-1-[(3-cyanophenyl)sulfonyl]-4-(octahydroisoquinolin-2(1H)-yl)-L-prolyl-4-[(3,5-dichloroisonicotinoyl)amino]-L-phenylalanine and ethyl ester thereof;

(4R)-4-(2-azabicyclo[2.2.2]oct-2-yl)-1-[(3-cyanophenyl)sulfonyl]-L-prolyl-4-[(3,5-dichloroisonicotinoyl)amino]-L-phenylalanine and methyl ester thereof;

and pharmaceutically acceptable salts thereof.

In another aspect the present invention provides a method for the prevention or treatment of diseases, disorders, conditions or symptoms mediated by cell adhesion in a mammal which comprises administering to said mammal an effective amount of a compound of formula I. This aspect includes the use of a compound of formula I in the manufacture of a medicament for the treatment of diseases, disorders, conditions or symptoms mediated by cell adhesion in a mammal. In one embodiment said disease or disorder is selected from asthma, allergic rhinitis, multiple sclerosis, atherosclerosis, inflammatory bowel disease, rheumatoid arthritis, organ transplantation, acute leukemia, and sickle cell anemia. In another embodiment, the method provides for the prevention or treatment of heaves in horses. In yet another embodiment, the method provides for the prevention or treatment of arthritis in dogs.

In another aspect the present invention provides a method for preventing the action of VLA-4 in a mammal which comprises administering to said mammal a therapeutically effective amount of a compound of formula I. This aspect includes the use of a compound of formula I in the manufacture of a medicament for preventing the action of VLA-4 in a mammal.

Another aspect of the present invention provides a pharmaceutical composition which comprises a compound of formula I and a pharmaceutically acceptable carrier.

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic saturated carbocyclic rings, each of which having from 3 to 10 carbon atoms. The term also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl, and the like.

"Aryl" means mono- or bicyclic aromatic rings containing only carbon atoms. The term also includes aryl group fused to a monocyclic cycloalkyl or monocyclic heterocyclyl group in which the point of attachment is on the aromatic portion. Examples of aryl include phenyl, naphthyl, indanyl, indenyl, tetrahydronaphthyl, 2,3-dihydrobenzofuranyl, dihydrobenzopyranyl, 1,4-benzodioxanyl, and the like.

"Heteroaryl" means a mono- or bicyclic aromatic ring containing at least one heteroatom selected from N, O and S, with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, and the like.

"Heterocyclyl" means mono- or bicyclic saturated rings containing at least one heteroatom selected from N, S and O, each of said ring having from 3 to 10 atoms in which the point of attachment may be carbon or nitrogen. The term also includes monocyclic heterocycle fused to an aryl or heteroaryl group in which the point of attachment is on the non-aromatic portion. Examples of "heterocyclyl" include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

"Halogen" includes fluorine, chlorine, bromine and iodine.

Optical Isomers—Diastereomers—Geometric Isomers—Tautomers

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example MeOH or EtOAc or a mixture thereof. The pair of enantiomers thus obtained may be separated into individual stereoisomers by conventional means, for example by the use of an optically active amine as a resolving agent or on a chiral HPLC column.

Alternatively, any enantiomer of a compound of the general Formula I or Ia may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic nontoxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Utilities

The ability of the compounds of Formula I to antagonize the actions of VLA-4 integrin makes them useful for preventing or reversing the symptoms, disorders or diseases induced by the binding of VLA-4 to its various ligands. Thus, these antagonists will inhibit cell adhesion processes including cell activation, migration, proliferation and differentiation. Accordingly, another aspect of the present invention provides a method for the treatment (including prevention, alleviation, amelioration or suppression) of diseases or disorders or symptoms mediated by VLA-4 binding and cell adhesion and activation, which comprises administering to a mammal an effective amount of a compound of Formula I. Such diseases, disorders, conditions or symptoms are, for example (1) multiple sclerosis, (2) asthma, (3) allergic rhinitis, (4) allergic conjunctivitis, (5) inflammatory lung diseases including chronic obstructive pulmonary disease, (6) rheumatoid arthritis, (7) septic arthritis, (8) type I diabetes, (9) organ transplantation rejection, (10) restenosis, (11) autologous bone marrow transplantation, (12) inflammatory sequelae of viral infections, (13) myocarditis, (14) inflammatory bowel disease including ulcerative colitis and Crohn's disease, (15) certain types of toxic and immune-based nephritis, (16) contact dermal hypersensitivity, (17) psoriasis, (18) tumor metastasis, (19) atherosclerosis, (20) sickle cell anemia, (21) certain acute leukemias, (22) various melanomas, carcinomas and sarcomas (including multiple myeloma); (23) acute respiratory distress syndrome; (24) uveitis; (25) circulatory shock; and (26) hepatitis. These diseases may occur in humans as well as in animals, and an animal disorder may be known by a different name; for example, heaves is a airway obstruction disease in horses which is also variously known as COPD or recurrent airway obstruction disease. Compounds of formula I are useful in the treatment of VLA-4 mediated diseases in humans as well as in non-human animals such as horses, cats and dogs.

The utilities of the present compounds in these diseases or disorders may be demonstrated in animal disease models that have been reported in the literature. The following are examples of such animal disease models: i) experimental allergic encephalomyelitis, a model of neuronal demyelination resembling multiple sclerosis (for example, see T. Yednock et al., *Nature,* 356, 63 (1993) and E. Keszthelyi et al., *Neurology,* 47, 1053 (1996)); ii) bronchial hyperresponsiveness in sheep and guinea pigs as models for the various phases of asthma (for example, see W. M. Abraham et al., *J. Clin. Invest.* 93, 776 (1993) and A. A. Y. Milne and P. P. Piper, *Eur. J. Pharmacol.,* 282, 243 (1995)); iii) adjuvant-induced arthritis in rats as a model of inflammatory arthritis (see C. Barbadillo et al., *Arthr. Rheuma.* (Suppl.), 36 95 (1993) and D. Seiffge, *J. Rheumatol.,* 23, 12 (1996)); iv) adoptive autoimmune diabetes in the NOD mouse (see J. L. Baron et al., *J. Clin. Invest.,* 93, 1700 (1994), A. Jakubowski et al., *J. Immunol.,* 155, 938 (1995), and X. D. Yang et al., *Diabetes,* 46, 1542 (1997)); v) cardiac allograft survival in mice as a model of organ transplantation (see M. Isobe et al., *Tranplant. Proc.,* 26, 867 (1994) and S. Molossi et al., *J. Clin Invest.,* 95, 2601 (1995)); vi) spontaneous chronic colitis in cotton-top tamarins which resembles human ulcerative colitis, a form of inflammatory bowel disease (see D. K. Podolsky et al., *J. Clin. Invest.,* 92, 372 (1993)); vii) contact hypersensitivity models as a model for skin allergic reactions (see T. A. Ferguson and T. S. Kupper, *J. Immunol.,* 150, 1172 (1993) and P. L. Chisholm et al., *Eur. J. Immunol.,* 23, 682 (1993)); viii) acute nephrotoxic nephritis (see M. S. Mulligan et al., *J. Clin. Invest.,* 91, 577 (1993)); ix) tumor metastasis (for examples, see M. Edward, *Curr. Opin. Oncol.,* 7, 185 (1995)); x) experimental autoimmune thyroiditis (see R. W. McMurray et al., *Autoimmunity,* 23, 9 (1996); xi) ischemic tissue damage following arterial occlusion in rats (see F. Squadrito et al., *Eur. J. Pharmacol.,* 318, 153 (1996)); xii) inhibition of TH2 T-cell cytokine production including IL-4 and IL-5 by VLA-4 antibodies which would attenuate allergic responses (*J. Clinical Investigation* 100, 3083 (1997); xiii) antibodies to VLA-4 integrin mobilize long term repopulating cells and augment cytokine-induced mobilization in primates and mice (*Blood,* 90 4779-4788 (1997); xiv) sickle reticulocytes adhere to VCAM-1 (Blood 85 268-274 (1995) and *Blood* 88 4348-4358 (1996); xv) chemokine stromal cell derived factor 1 modulates VLA-4 integrin mediated multiple myeloma cell adhesion to CS-1/fibronectin and VCAM-1 (*Blood,* 97, 346-351 2001)

Dose Ranges

The magnitude of prophylactic or therapeutic dose of a compound of Formula I will, of course, vary with the nature and severity of the condition to be treated, and with the particular compound of Formula I used and its route of administration. The dose will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.01 mg to about 25 mg (preferably from 0.1 mg to about 10 mg) of a compound of Formula I per kg of body weight per day.

In the case where an oral composition is employed, a suitable dosage range is, e.g. from about 0.01 mg to about 100 mg of a compound of Formula I per kg of body weight per day, preferably from about 0.1 mg to about 10 mg per kg.

For use where a composition for sublingual administration is employed, a suitable dosage range is from 0.01 mg to about 25 mg (preferably from 0.1 mg to about 5 mg) of a compound of Formula I per kg of body weight per day.

For the treatment of asthma, a compound of Formula I may be used at a dose of from about 0.1 mg/kg to about 100 mg/kg, preferably from about 1 mg/kg to 10 mg/kg, by oral/inhalation/sublingual/etc. once, twice, three times daily, etc. The dose may be adminstered as a single daily dose or divided for twice or thrice daily administration.

For the treatment of multiple sclerosis, a compound of Formula I may be used at a dose of from about 0.1 mg/kg to about 100 mg/kg, preferably from about 1 mg/kg to 10 mg/kg, by oral/inhalation/sublingual/etc. once, twice, three times daily, etc. The dose may be adminstered as a single daily dose or divided for twice or thrice daily administration.

For the treatment of inflammatory bowel disease, a compound of Formula I may be used at a dose of from about 0.1 mg/kg to about 100 mg/kg, preferably from about 1 mg/kg to 10 mg/kg, by oral/inhalation/etc. once, twice, three times daily, etc. The dose may be adminstered as a single daily dose or divided for twice or thrice daily administration.

For the treatment of rheumatoid arthritis, a compound of Formula I may be used at a dose of from about 0.1 mg/kg to about 100 mg/kg, preferably from about 1 mg/kg to 10 mg/kg, by oral/inhalation/sublingual/etc. once, twice, three times daily, etc. The dose may be adminstered as a single daily dose or divided for twice or thrice daily administration.

Pharmaceutical Compositions

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, especially a human with an effective dosage of a compound of the present invention. For example, oral, sublingual, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, sublingual, rectal, topical, parenteral (including subcutaneous, intramuscular, and intravenous), ocular (ophthalmic), pulmonary (inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulizers. The compounds may also be delivered as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

The following are examples of representative pharmaceutical dosage forms for the compounds of Formula I:

| Inj. Suspension (I.M.) | mg/mL |
|---|---|
| Cmpd of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tab. |
|---|---|
| Cmpd of Formula I | 25 |
| Microcryst. Cellulose | 415 |
| Povidone | 14.0 |
| Pregelatinized Starch | 43.5 |
| Magnesium Stearate | 2.5 |
| | 500 |

-continued

| Capsule | mg/cap. |
| --- | --- |
| Cmpd of Formula I | 25 |
| Lactose Powder | 573.5 |
| Magnesium Stearate | 1.5 |
| | 600 |

| Aerosol | Per canister |
| --- | --- |
| Compound of Formula I | 24 mg |
| Lecithin, NF Liq. Conc. | 1.2 mg |
| Trichlorofluoromethane, NF | 4.025 g |
| Dichlorodifluoromethane, NF | 12.15 g |

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to: (a) other VLA-4 antagonists such as those described in U.S. Pat. No. 5,510,332, WO97/03094, WO97/02289, WO96/40781, WO96/22966, WO96/20216, WO96/01644, WO96/06108, WO95/15973 and WO96/31206, as well as natalizumab; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, salmeterol and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors such as celecoxib, rofecoxib, and parecoxib; (h) inhibitors of phosphodiesterase type IV (PDE-IV); (i) antagonists of the chemokine receptors, especially CCR-1, CCR-2, and CCR-3; () cholesterol lowering agents such as HMG-CoA reductase inhibitors (lovastatin, simvastatin, pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone, pioglitazone, englitazone, MCC-555, BRL49653 and the like); (l) preparations of interferon beta (interferon beta-1a, interferon beta-1b); (m) anticholinergic agents such as muscarinic antagonists (ipratropium and tiatropium); (n) current treatments for multiple sclerosis, including prednisolone, glatiramer, deoxyadenosine, mitoxantrone, methotrexate, and cyclophosphamide; (o) p38 kinase inhibitors; (p) other compounds such as 5-aminosalicylic acid and prodrugs thereof, antimetabolites such as azathioprine and 6-mercaptopurine, and cytotoxic cancer chemotherapeutic agents.

The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Abbreviations that may be used in the following Schemes and Examples include: 4-DMAP: 4-dimethylaminopyridine; AcCN: acetonitrile; BOC: tert-butoxycarbonyl; BOC-ON:2-(tert-butoxycarbonyloxyimino)-2-phenylacetonitrile; BOP: benzotriazol-1-yloxy-tris(dimethylamino)-phosphonium hexafluorophosphate; brine: saturated NaCl solution; DIPEA: N,N-diisopropylethylamine; DMF: dimethylformamide; DMSO: dimethylsulfoxide; Et: ethyl; EtOAc: ethyl acetate; EtOH: ethanol; g or gm: gram; h or hr: hours; HATU: O-(7-azabenzotriazol-1-yl)-1,1,3,3-tetramethyluronium hexafluorophosphate; HBTU: O-(benzotriazol-1-yl)-1,1,3,3-tetramethyluronium hexafluorophosphate; HOAc: acetic acid; HOAt: 1-hydroxy-7-azabenzotriazole; HOBt: 1-hydroxybenzotriazole; IPLC: high pressure liquid chromatography; in vacuo: rotoevaporation; Me: methyl; MeOH: methanol; mg: milligram; MHz: megahertz; min: minutes; mL: milliliter; mmol: millimole; MS or ms: mass spectrum; MsCl: methanesulfonyl chloride; Ph: phenyl; $Ph_3P$: triphenylphosphine; PyBOP: (benzotriazol-1-yloxy)tripyrrolidino-phosphonium hexafluorophosphate; rt: room temperature; TEA: triethylamine; TFA: trifluoroacetic acid; TBF: tetrahydrofuran.

Compounds of the present invention may be prepared by procedures illustrated in the accompanying schemes. In Scheme 1, a substituted pyridyl-4-carboxylic acid derivative A is treated with thionyl chloride to make the carboxylic acid chloride derivative which is then reacted with a 4-amino-(L)-phenylalanine derivative to yield the amide B. The N-BOC-protecting group in B is removed with strong acid (TFA or HCl) to afford the free amine C.

Scheme 1

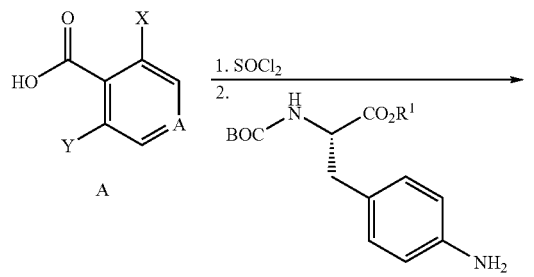

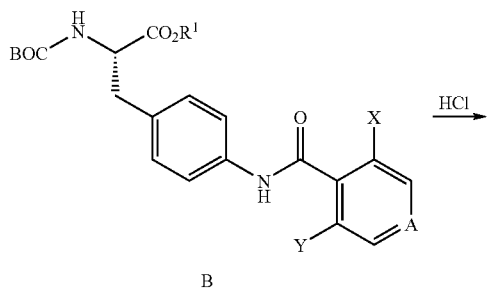

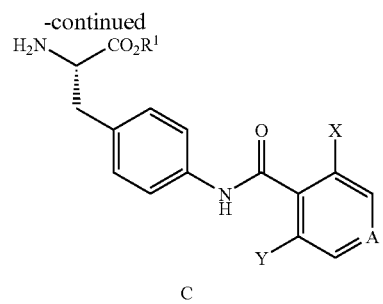

In Scheme 2, an appropriately substituted (L)-proline ester D (R'=H) is sulfonylated with 3-cyano-benzenesulfonyl chloride L in the presence of base (DIPEA or $Na_2CO_3$) to yield sulfonamide E which, if containing an ester protecting group, is treated with hydroxide to afford the free acid. Amine C and acid E are reacted together in the presence of an appropriate coupling agent (eg., PyBOP, HBTU/HOAt, or E may be first converted to the corresponding acid chloride) to afford amide F. Alternatively, the proline ester D (R'=BOC) is hydrolyzed to the corresponding acid by treatment with a base such as LiOH. The acid is then coupled with C, as described above, to give M, following the removal of the BOC group. The amine M and is then sulfonylated with L in the presence of a base to provide F. The ester in F can be hydrolyzed with hydroxide (if $R^1$ is n- or i-alkyl) or TFA or HCl (if $R^1$ is tert-butyl) to afford the corresponding acid.

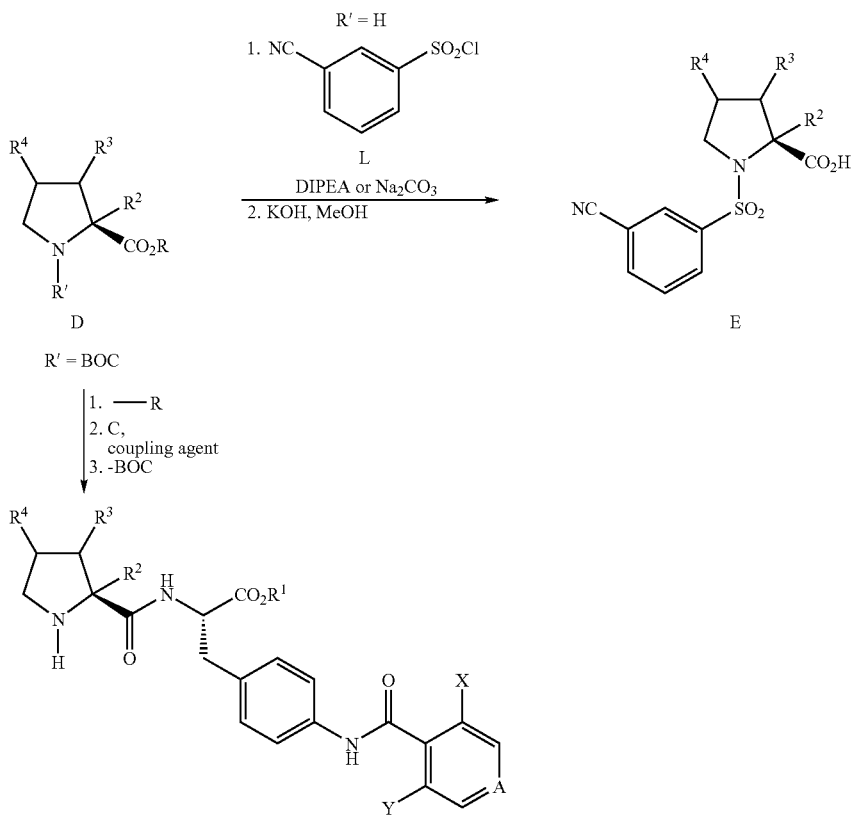

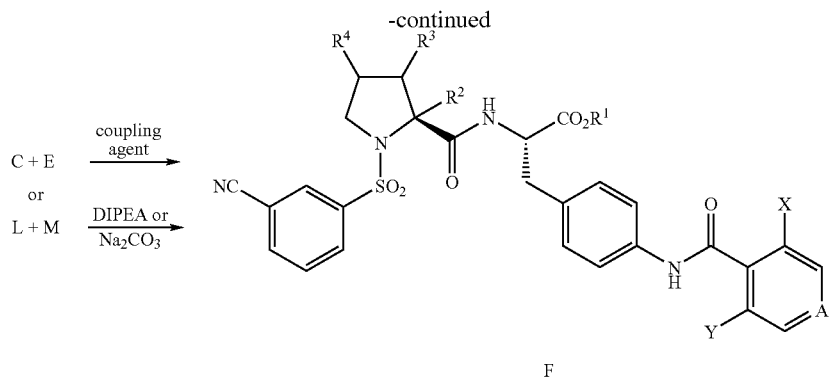

Biological Evaluation

Compounds of formula I are potent antagonists of VLA-4 with significant and sustained receptor occupancy on VLA-4 bearing cells. The rate of dissociation of a test compound from VLA-4 on Jurkat cells may be determined by the method described in G. Doherty et al., *Bioorganic & Medicinal Chemistry Letters*, 13, 1891 (2003). Compounds of the present invention had half-lives of dissociation of greater than three hours ($t_{1/2} > 3$ hr) in this assay, demonstrating they are tight binding inhibitors of VLA-4.

VLA-4 receptor occupancy after oral dosing in rats and dogs may be determined by the method described in D. R. Leone et al., *J. Pharmacol. Exper. Therap.*, 305, 1150 (2003). Compounds of the present invention demonstrated sustained and significant receptor occupancy (>50%) after oral dosing.

Compounds of the present invention may be prepared by procedures detailed in the following examples. The examples provided are illustrative of the present invention and are not to be construed as limiting its scope in any manner:

REFERENCE EXAMPLE 1

4-((3',5'-Dichloroisonicotinoyl)amino)-(L)-phenylalanine, Ethyl Ester, HCl

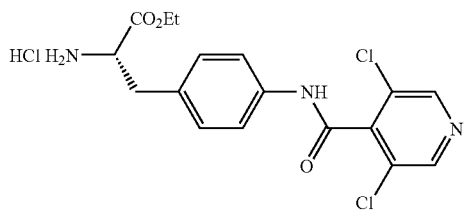

Step A: To 500 mL of absolute ethanol under nitrogen at 0° C. was added thionyl chloride (21 mL, 0.29 mol) over 5 min, and the clear solution was stirred at 0° C. for 10 min and then at rt for 30 min. 4-Nitro-L-phenylalanine (50.2 g, 0.24 mol) was added in one portion, and the mixture was refluxed overnight. The resulting mixture was concentrated in vacuo to give 4-nitro-L-phenylalanine, ethyl ester, HCl (60 g) as a white solid. $^1$H NMR (400 MHz, CD$_3$OD) δ 8.21 (d, 2H), 7.54 (d, 2H), 4.39 (dd, 1H), 4.22 (q, 2H), 3.24-3.40 (m, 2M), 1.22 (t, 3H).

Step B: To a suspension of the compound of Step A (60 g, 0.22 mol) in methylene chloride (1.5 L) under nitrogen was added TEA (31 mL). After stirring at rt for 10 min, di-t-butyl dicarbonate (49 g, 0.22 mol) and 4-DMAP (0.1 g) was added, and the reaction mixture was stirred at rt overnight, washed with 1N HCl (2×200 mL), H$_2$O (2×200 mL) and brine (1×250 mL), dried over anhydrous Na$_2$SO$_4$, filtered and concentrated to afford N—BOC-4-nitro-L-phenylalanine, ethyl ester (78 g). $^1$H NMR (400 MHz, CDCl$_3$) δ 8.14 (d, 2H), 7.28 (d, 2H), 4.30-4.65 (m, 1H), 4.15 (q, 2H), 3.00-3.30 (m, 2H), 1.35 (s, 9H), 1.20 (t,3H).

Step C: A solution of the compound of Step B (78.3 g, 0.22 mol) in absolute ethanol (300 mL) was purged with nitrogen, and 10% palladium on carbon (1.0 g) was added. After hydrogenated at 40-50 psi for 1 h, the reaction mixture was filtered through Celite, and the cake was washed with EtOH followed by EtOAc. The filtrate was concentrated, and the residue was purified by flash column chromatography on silica gel eluting with 4:1 to 1:1 EtOAc/Hexanes to afford N—BOC-4-amino-L-phenylalanine, ethyl ester (60 g). $^1$H NMR (400 MHz, CDCl$_3$) δ 6.90 (d, 2H), 6.63 (d, 2H), 4.20-4.50 (m, 1H), 4.14 (q, 2H), 3.76-3.00 (m, 2H), 1.36 (s, 9H), 1.20 (t, 3H).

Step D: A nitrogen flushed 500 mL round bottom flask was charged with 3,5-dichloroisonicotinic acid (46.5 g, 0.24 mol), CH$_2$Cl$_2$ (150 mL), DMF (0.5 mL), and thionyl chloride (20 mL, 33.9 g 0.28 mol). After the slurry was refluxed for 5 h, additional thionyl chloride (5 mL, 0.70 mol) and CH$_2$Cl$_2$ (100 mL) were added, and the reaction mixture was refluxed for additional 45 min and concentrated, and the residue was azeotroped with toluene to give the crude acyl chloride, which was used immediately. The crude acyl chloride was dissolved in CH$_2$Cl$_2$ (150 mL) and added to the compound of Step C (60 g, 0.20 mol) and 4-methylmorpholine (44 mL, 0.40 mol) in CH$_2$Cl$_2$ (400 mL) at 0° C. over 5 min. After stirring at 0° C. for 1 h, the reaction was quenched with dilute aqueous NaHCO$_3$. The organic layer was separated and the aqueous layer was extracted with CH$_2$Cl$_2$ (500 mL). The organic layers were combined, dried over anhydrous MgSO$_4$ and concentrated in vacuo, and the residue was purified by flash column chromatography on silica gel eluting with 4:1 to 3:2 EtOAc/hexanes to afford N—BOC-4-((3',5'-dichloroisonicotinoyl)amino)-L-phenylalanine, ethyl ester (95 g). $^1$H NMR (400 MHz, CD$_3$OD) δ 8.60 (s, 2H), 7.54 (d, 2H), 7.20 (d, 2H), 4.20-4.36 (m, 1H), 4.10 (q, 2H), 3.02-3.12 (m, 1H), 2.82-2.92 (m, 1H), 1.34/1.30 (s, 9H),1.20 (t, 3H).

Step E: A solution of the compound of Step D (95 g, 0.197 mol) in EtOAc (1.2 L) was treated with a stream of hydrogen chloride gas over 2 h at rt. The resulting yellow suspension was diluted with hexanes (250 mL), cooled to 0° C. and filtered. The cake was washed with hexanes and dried in vacuo to afford the title compound as a yellow solid (80 g). $^1$H NMR (400 MHz, CD$_3$OD) δ 8.64 (s, 2H), 7.66 (d, 2H), 7.30 (d, 2H), 4.28 (dd, 1H), 4.25 (q, 2H), 3.20 (q, 2H), 1.26 (t, 3H).

REFERENCE EXAMPLE 2

N—BOC-cis-4-hydroxy-L-proline methyl ester

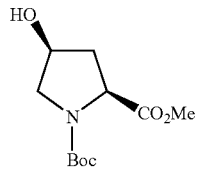

Step A. A mixture of trans-4-hydroxy-L-proline (72.8 g, 0.56 mol), 2.5 M NaOH (480 mL, 1.20 mol, 2.18 eq), THF (100 mL), and di-tert-butyl dicarbonate (128 g, 0.58 mol, 1.07 eq) was stirred overnight at room temperature. The resulting white suspension was cooled to 0° C., acidified with conc HCl (105 mL, 1.26 mol, 2.29 eq), and extracted with CH$_2$Cl$_2$ (1×1L, 3×0.5 L) and ethyl acetate (2×1L). The combined organic extracts were dried with MgSO$_4$, filtered and concentrated affording N-Boc-trans-4-hydroxy-L-proline as a viscous oil (146.3 g). The crude product (144.5 g, theory 0.56 mol), methyl iodide (100 mL, 1.6 mol, 2.90 eq), potassium carbonate (110 g, 0.8 mol, 1.42 eq) and acetone (2.5 L) were combined and the mixture refluxed for 4 hr. The reaction was allowed to cool to room temperature and stirred overnight. The mixture was filtered and the cake washed with acetone. The filtrate was concentrated, the residue dissolved in EtOAc containing a little CH$_2$Cl$_2$ and washed with brine, dried with MgSO$_4$, filtered and concentrated affording a white slurry. The slurry was flushed with hexanes, cooled to 0° C., and filtered. The cake was dried affording 121.7 g of N-Boc-trans-4-hydroxy-L-proline methyl ester as a white solid.

Step B. The compound of Step A (144.5 g, 0.59 mol), triphenyl phosphine (200 g, 0.76 mol, 1.29 eq), p-nitrobenzoic acid (150 g, 0.9 mol, 1.52 eq) and THF (2.5 L) were mixed and cooled to 0° C. Diethyl diazodicarboxylate (120 mL, 0.76 mol, 1.29 eq) was added over 10 min. The reaction exothermed to 30° C. and was allowed to cool to room temperature and stir overnight. The reaction was concentrated, the residue diluted with ether (1L) and the resulting suspension filtered. The filtrate was again concentrated, re-dissolved in CH$_2$Cl$_2$ and chromatographed (silica, linear gradient CH$_2$Cl$_2$ to 5% EtOAc/CH$_2$Cl$_2$). The product cuts were combined and concentrated. The concentrate was flushed with ether then hexanes to afford a white slurry which was filtered and dried giving 218.7 g of the title compound as a white solid.

REFERENCE EXAMPLE 3

Methyl (4S)-1-[(3-Cyanophenyl)sulfonyl]-4-hydroxyprolinate

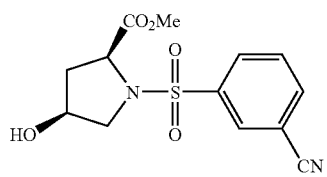

Methyl (4S)-4-hydroxyprolinate (52.0 g, 0.286 mol) was dissolved in 500 mL CH$_2$Cl$_2$ and cooled to 0° C. Triethylamine (83.6 mL, 0.600 mol) was added, followed by 3-cyanobenzenesulfonyl chloride (55.0, 0.273 mol) slowly. The reaction mixture was stirred at room temperature overnight. Water was added, and the aqueous layer was extracted three times with CH$_2$Cl$_2$. The combined organic layers were washed with 1N HCl, H$_2$O, 1N NaOH, and brine, dried over MgSO$_4$, and concentrated to give a viscous residue. Ethyl acetate (300 mL) was added to completely dissolve the residue. Approximately 100 mL hexanes was added slowly until the solution became slightly cloudy. The mixture was then stirred overnight to allow the product to precipitate. The solid was filtered and rinsed two times with 30% EtOAc/hexanes to give the desired product as an off-white powder (66.2 g, 78%). $^1$H-NMR (CDCl$_3$, 500 MHz) δ 8.20-8.18 (m, 1H), 8.15-8.12 (m, 1H), 7.92-7.89 (m, 1H), 7.72 (t, 1H), 4.51-4.47 (m, 1H), 4.42 (br s, 1H), 3.74 (s, 3H), 3.53-3.49 (m, 1H), 3.46-3.43 (m, 1H), 3.39 (br s, 1H), 2.29-2.25 (m, 1H), 2.21-2.02 (m, 1H). MS (ESI) calculated for C$_{13}$H$_{14}$N$_2$O$_5$S 310.3, observed m/e 311.2 (MH$^+$).

EXAMPLE 1

N-{N-[(3-Cyanobenzene)sulfonyl]-4(R)-cyclobutylamino-(L)-prolyl}-4-[(3',5'-dichloroisonicotinoyl)-amino]-(L)-phenylalanine

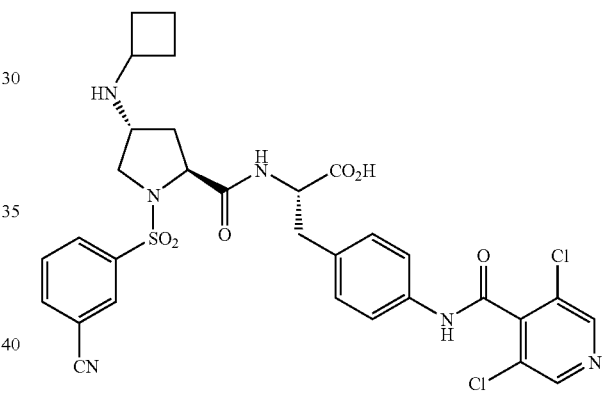

Step A: To a solution of N—BOC-cis-4-hydroxy-L-proline methyl ester (60 g, 0.25 mol) and DIPEA (100 mL, 0.57 mol) in methylene chloride (800 mL) at −20° C. was added trifluoromethanesulfonic anhydride over 45 min. After stirring at −20° C. for additional 45 min, cyclobutylamine (55 g, 0.78 mol) was added in one portion, and the reaction was allowed to warm up to rt overnight. The reaction was quenched with 1N NaOH (250 mL) and saturated aqueous NaHCO$_3$ (250 mL). The organic layer was separated, washed with brine, dried with MgSO$_4$, filtered and concentrated, and the residue was purified by flash column chromatography on silica gel eluting with CH$_2$Cl$_2$ to EtOAc to 5% MeOH/EtOAc) to afford N—BOC-4(R)-cyclobutylamino-L-proline, methyl ester (77 g). $^1$H NMR (400 MHz, CD$_3$OD) δ 4.8 (br s, 1H), 4.24-4.32 (m, 1H), 3.67/3.68 (s, 3H), 3.56-3.64 (m, 1H), 3.1-3.38 (m, 3H), 2.12-2.21 (m, 2H), 2.00-2.12 (m, 2H), 1.54-1.82 (m, 4H), 1.36/1.43 (s, 9H).

Step B: To a solution of the compound of Step A (77 g, 0.25 mol) in CH$_3$CN (350 mL) and water (150 mL) was added LiOH monohydrate (21 g, 0.50 mol), and the suspension was stirred at rt overnight. The reaction mixture was diluted to a total volume of 1 L with CH$_3$CN, cooled to 0° C. and filtered, and the filtrate was obtained as a solution of the lithium salt of N—BOC-4(R)-cyclobutylamino-(L)- proline. A portion of the above filtrate (484 mL, 0.22 M, 0.11 mol) was concentrated, and to the residue was added water (1 L), CH$_2$Cl$_2$ (1 L), EDC (20.8 g, 0.11 mol), HOBt (14.6 g, 0.11 mol) and a solution of 4-((3,',5'-dichloroisonicotinoyl)amino)-(L)-phenylalanine ethyl ester HCl (39 g, 0.090 mol) in water (1 L). The biphasic mixture was stirred vigorously at rt for 4 h. The organic layer was separated and the aqueous layer was extracted with CH$_2$Cl$_2$ (0.5 L). The combined organic layers were dried over Na$_2$SO$_4$, filtered and concentrated, and the residue was purified by flash column chromatography on silica gel eluting with EtOAc to EtOAc/MeOH/NH$_4$OH (98:1:1) to afford N-[N—BOC-4(R)-cyclobutylamino-(L)-prolyl]-4-[(3',5'-dichloroisonicotinoyl)amino]-(L)-phenylalanine, ethyl ester (48 g). $^1$H NMR (400 MHz, CD$_3$OD) δ 8.64 (s, 2H), 7.57 (d, 2H), 7.20-7.30 (m, 2H), 4.80 (br s, 1H), 4.58-4.70 (m, 1H), 4.08-4.30 (m, 3H), 3.56-3.64 (m, 1H), 2.90-3.30 (m, 5H), 3.00-3.08 (m, 1H), 1.5-2.2 (m, 8H), 1.22 (br s, 9H), 1.2 (t, 3H).

Step C: To a solution of the compound of Step B in ethanol (300 mL) was added 4 M HCl in dioxane (250 mL). After stirring at rt overnight, the clear yellow solution was concentrated, and the residue was triturated with ether (1 L). The resulting suspension was stirred for at rt for 2 h, and the precipitate was collected by filtration. The cake was washed with ether and dried to afford N-[4(R)-cyclobutylamino-(L)-prolyl]-4-[(3',5'-dichloroisonicotinoyl)amino]-(L)-phenylalanine, ethyl ester, HCl (45.6 g). $^1$H NMR (400 MHz, CD$_3$OD) δ 8.86 (d, 1H), 8.62 (s, 2H), 7.58 (d, 2H), 7.26 (d, 2H), 4.80 (br s, 1H), 4.70 (m, 1H), 4.64 (dd, 1H), 4.15 (q, 2H), 3.80-3.95 (m, 3H), 3.5 (dd, 1H), 3.24 (dd, 1H), 3.00 (dd, 1H), 2.50-2.70 (m, 2H), 2.20-2.40 (m, 4H), 1.8-2.0 (m, 2H), 1.22 (t, 3H).

Step D: To a suspension of the compound of Step C (18 g, 30 mmol), 3-cyanobenzenesulfonyl chloride (6.0 g, 30 mmol), 4-DMAP (50 mg) in THF (80 mL) and methylene chloride (80 mL) at 0° C. was added DIPEA (21 mL, 0.12 mol). The reaction mixture was allowed to warm up to rt over 3 h, and the resulting mixture was concentrated. The residue was dissolved in EtOAc (400 mL), washed with 1 N NaOH and brine and concentrated to dryness. The residue was purified by flash column chromatography on silica gel with 2 N ammonia in MeOH/EtOAc (0 to 3%) to give N-{N-[(3-cyanobenzene)sulfonyl]-4(R)-cyclobutylamino-(L)-prolyl}-4-[(3',5'-dichloroisonicotinoyl)amino]-(L)-phenylalanine, ethyl ester (18 g). $^1$H NMR (500 MHz, CD$_3$OD): δ 8.64 (s, 2H), 8.19 (m, 1H), 8.00-8.04 (m, 2H), 7.72 (dd, 1H), 7.63 (d, 2H), 7.32 (d, 2H), 4.70 (dd, 1H), 4.28 (dd, 1H), 4.20 (q, 2H), 3.60 (dd, 1H), 3.30 (m, 1H), 3.25 (dd, 1H), 3.10 (m, 1H), 3.06 (dd, 1H), 3.08 (dd, 1H), 2.07-2.14 (m, 2H), 1.98 (m, 1H), 1.75 (m, 1H), 1.60-1.66 (m, 4H), 1.27 (t, 3H). LC-MS: calculated for C33H34Cl2N6O6S 712, observed m/e 713 (M+H)$^+$ (2.8 min).

To a sample of the above compound (5.6 g) in 100 mL of ethanol was added methanesulfonic acid (1.1 eq). Ether was then added until the solution turned cloudy. After stirring at rt for 6 h, the crystals were collected by filtration to give the methanesulfonic acid salt of the above ester. $^1$H NMR (500 MHz, CD$_3$OD): δ 8.64 (s, 2H), 8.30 (s, 1H), 8.02 (dd, 1H), 7.82 (d, 1H), 7.64-7.71 (m, 3H), 7.36 (d, 2H), 4.63 (dd, 1H), 4.56 (dd, 1H), 4.18 (m, 2H), 3.88 (m, 1H), 3.76-3.83 (m, 2H), 3.44 (dd, 1H), 3.24 (dd, 1H), 3.04 (dd, 1H), 2.70 (s, 3H), 2.30-2.38 (m, 3H), 2.13-2.24 (m, 3H) 1.90-1.96 (m, 2H), 1.26 (t, 3H). LC-MS: calculated for C33H34Cl2N6O6S 712, observed m/e 713 (M+H)$^+$ (2.9 min).

Step E: To a solution of the compound of Step D (free amine, 23 g, 32 mmol) in 80 mL of AcCN and 40 mL of water was added LiOH monohydrate (2.7 g, 65 mmol). After stirring at rt for 2 h, the reaction was quenched with aqueous formic acid (98%, 2.4 mL, 65 mmol). The reaction was diluted with water (20 mL) and was stirred at rt overnight. The crystals formed were collected by filtration to give the title compound (18 g). $^1$H NMR (500 MHz, CD$_3$OD): δ 8.63 (s, 2H), 8.15 (s, 1H), 8.00 (dd, 1H), 7.88 (dd, 1H), 7.69 (t, 1H), 7.62 (d, 2H), 7.36 (d, 2H), 4.44-4.50 (m, 2H), 3.68-3.73 (m, 1H), 3.62-3.66 (m, 1H), 3.50-3.58 (m, 1H), 3.20-3.29 (m, 2H), 3.12 (dd, 1H), 2.20-2.32 (m, 3H), 1.92-2.00 (m, 3H), 1.76-1.84 (m, 2H). LC-MS: calculated for C31H30Cl2N6O6S 684, observed m/e 685 (M+H)$^+$ (2.6 min).

To a sample of the above compound (1.2 g) in 20 mL of water and AcCN (3:1) was added methanesulfonic acid (1.1 eq). The mixture was lyophilized, and the solid residue was crystallized in AcCN to give the title compound as the methanesulfonic acid salt. $^1$H NMR (500 MHz, CD$_3$OD): δ 8.64 (s, 2H), 8.54 (br d, 1H), 8.08 (s, 1H), 8.00 (br d, 1H), 7.76 (br d, 1H), 7.66 (d, 2H), 7.65 (t, 1H), 7.38 (d, 2H), 4.64 (br d, 1H), 4.56 (m, 1H), 3.90-3.73 (m, 3H), 3.44 (dd, 1H), 3.28 (dd, 1H), 3.00 (dd, 1H), 2.70 (s, 3H), 2.39-2.30 (m, 3H), 2.24-2.12 (m, 3H), 1.96-1.89 (m, 2H). LC-MS: calculated for C31H30Cl2N6O6S 684, observed m/e 685 (M+H)$^+$ (2.6 min).

EXAMPLE 2

N-{N-[(3-Cyanobenzene)sulfonyl]-3(S)-tert-butylamino-(L)-prolyl}-4-[(3',5'-dichloroisonicotinoyl)-amino]-(L)-phenylalanine (R$^1$═H), ethyl ester (R$^1$═CH$_2$CH$_3$), pivaloyloxymethyl ester (R$^1$═—CH$_2$OC(O)C(CH$_3$)$_3$), and 1-(ethoxycarbonyloxy) ethyl ester (R$^1$═—CH(CH$_3$)OC(O)OCH$_2$CH$_3$)

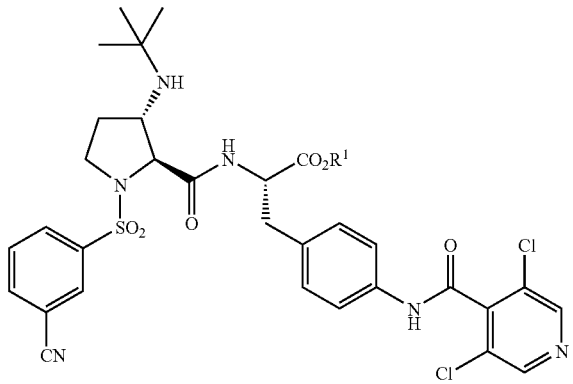

Step A: To a solution of (3S)-hydroxy-(L)-proline (Acros, 20 g, 0.15 mol) and sodium carbonate (26 g, 0.25 mol) in 500 mL of water at 0° C. was added powdered 3-cyanobenzenesulfonyl chloride (25 g, 0.12 mol). After stirring at rt overnight, the reaction mixture was acidified with concentrated HCl (pH=3), and the product was extracted with EtOAc (3×100 mL). The organic extracts were dried (MgSO$_4$), filtered and concentrated to dryness. The residue was then dissolved in methylene chloride (100 mL) and MeOH (100 mL), and was added trimethylsilyldiazomethane (2 M in ether) at 0° C. until a yellow color persisted. After stirring at rt for 15 min, the mixture was concentrated to dryness to give N-[(3-cyanobenzene)sulfonyl]-3(S)-hydroxy-(L)-proline, methyl ester (31.5 g). LC-MS: calculated for C13H14N2O5S 310, observed m/e 311 (M+H)$^+$ (2.3 min).

Step B: To a solution of the compound of Step A (31.5 g, 0.10 mol) in 200 mL of EtOAc at 0° C. was added TEA (20 mL, 0.14 mol) and MsCl (9.5 mL, 0.12 mol). After stirring at 0° C. for 20 min, the reaction was quenched with 100 mL of aqueous sodium bicarbonate. After stirring for 15 min, the reaction mixture was partitioned between EtOAc (300 mL) and aqueous sodium bicarbonate (200 mL). The organic layer was separated, washed with brine and concentrated to dryness to give N-[(3-cyanobenzene)sulfonyl]-3(S)-methanesulfonyloxy-(L)-proline, methyl ester (40 g). LC-MS: calculated for C14H16N2O7S2 388, observed m/e 389 (M+H)$^+$ (2.7 min).

Step C: To a solution of the compound of Step B (39.5 g, 0.10 mol) in 300 mL of AcCN was added TEA (35 mL, 0.25 mol). After heating at 75° C. for 4 h, the reaction mixture was cooled to rt and concentrated. The residue was dissolved in EtOAc (600 mL) and washed with 1 N aqueous NaOH and brine, and concentrated to dryness to give N-[(3-cyanobenzene)sulfonyl]-2,3-dehydroproline, methyl ester (28 g). $^1$H NMR (500 MHz, CD$_3$OD): δ 8.22 (s, 1H), 8.17 (d, 1H), 8.05 (d, 1H), 7.80 (t, 1H), 6.35 (t, 1H), 3.98 (t, 2H), 3.81 (s, 3H), 2.14 (td, 2H), 8.63 (s, 2H). LC-MS: calculated for C13H12N2O4S 292, observed m/e 293 (M+H)$^+$ (2.7 min).

Step D: To a suspension of the compound of Step C (26.4 g, 90 mmol) in 225 mL of cyclohexane and 75 mL of tert-butanol was added tert-butylamine (95 mL, 0.90 mol). After heating at 50° C. for 48 h, the reaction mixture was cooled to rt and was concentrated. The solid residue was triturated with hexane and collected by filtration to give N-[(3-cyanobenzene)sulfonyl]-3-tert-butylaminoproline, methyl ester as a racemic mixture (29 g). $^1$H NMR (400 MHz, CD$_3$OD): δ 8.24 (br s, 1H), 8.16 (br d, 1H), 8.03 (br d, 1H), 7.80 (dd, 1H), 3.99 (d, 1H), 3.75 (s, 3H), 3.45-3.55 (m, 2H), 3.33 (m, 1H), 2.17 (m, 1H), 1.62 (m, 1H), 0.97 (s, 9H). LC-MS: calculated for C17H23N3O4S 365, observed m/e 366 (M+H)$^+$ (1.9 min).

A sample of the above racemate (46 g, 0.13 mol) and (1R)-(10)-camphorsulfonic acid (29 g, 0.13 mol) was dissolved in hot AcCN (210 mL). After cooling to rt, the crystals were collected by filtration, which were recrystallized in AcCN to give 12.4 g of one pure enantiomer as the (1R)-(10)-camphorsulfonic acid salt. The pure (3S) enantiomer of the free base was obtained by stirring the (1R)-(10)-camphorsulfonic acid salt with EtOAc and 2 N aqueous NaOH followed by concentration of the organic layer. LC-MS: calculated for C17H23N3O4S 365, observed m/e 366 (M+H)$^+$ (1.9 min).

Step E: To a solution of the pure (3S) enantiomer of Step D (6.7 g, 18 mmol) in 100 mL of AcCN/water (2.5:1) was added LiOH monohydrate (2.0 g, 46 mol). After stirring at rt for 2.5 h, the reaction was quenched by addition of 2 N aqueous HCl (23 mL, 46 mmol), and the reaction mixture was lyophilized to give the crude lithium salt, which was used without further purification. To a suspension of the crude lithium salt in 70 mL of dry DMF was added 4-[(3', 5'-dichloroisonicotinoyl)amino]-(L)-phenylalanine ethyl ester hydrochloride salt (8.0 g, 19 mmol), PyBOP (11 g, 22 mmol) and N-methylmorpholine (6.0 mL, 55 mmol). After stirring at rt for 2.5 h, the reaction mixture was diluted with EtOAc (250 mL), washed with water (150 mL×2) and brine, dried over anhydrous magnesium sulfate, filtered and concentrated to dryness. The residue was purified by flash chromatography on silica gel to give the ethyl ester of the title compound (R$^1$=CH$_2$CH$_3$, 7.5 g). Crystals of the ethyl ester were obtained by recrystallization in AcCN. $^1$H NMR (500 MHz, CD$_3$OD): δ 8.63 (s, 2H), 8.23 (br s, 1H), 8.10 (br d, 1H), 8.03 (br d, 1H), 7.77 (t, 1H), 7.62 (d, 2H), 7.32 (d, 2H), 4.78 (m, 1H), 4.22 (q, 2H), 3.81 (d, 1H), 3.44 (m, 2H), 3.30-3.22 (m, 2H), 3.12 (dd, 1H), 1.83 (m, 1H), 1.43 (m, 1H), 1.31 (t, 3H), 0.91 (s, 9H). LC-MS: calculated for C33H36Cl2N6O6S 714, observed m/e 715 (M+H)$^+$ (2.9 min).

Step F: To a solution of the ethyl ester of Step E (2.0 g, 2.8 mmol) in 12 mL of AcCN and 6 mL of water was added NaOH (1 N, 7 mL, 7.0 mmol), and the reaction mixture was stirred at rt for 20 min. The reaction was quenched with 2 N HCl to pH=5, and was diluted with 200 mL of THF/EtOAc (1:3 v/v). The mixture was washed with water (50 mL) and concentrated to remove the organic solvents, and the residue was lyophilized to give the title acid compound (R$^1$=H, 1.9 g). $^1$H NMR (500 MHz, CD$_3$OD): δ 8.64 (s, 2H), 8.20 (br s, 1H), 7.99 (br d, 2H), 7.72 (t, 1H), 7.59 (d, 2H), 7.38 (d, 2H), 4.55 (m, 1H), 4.21 (br s, 1H), 3.69-3.61 (m, 2H), 3.39 (m, 2H), 3.25 (dd, 1H), 3.08 (dd, 1H), 2.17 (m, 1H), 1.72 (m, 1H), 1.18 (s, 9H). LC-MS: calculated for C31H32Cl2N6O6S 686, observed m/e 687 (M+H)$^+$ (2.7 min).

Pivaloylmethyl ester (R$^1$=—CH$_2$OC(O)C(CH$_3$)$_3$) A sample of the acid of Step F was converted to the sodium salt by treatment with 1 equivalent of NaOH followed by lyophilization. To a suspension of the sodium salt thus obtained (0.10 g, 0.14 mmol) in 0.5 mL DMSO was added chloroethyl pivalate (0.050 mL, 0.35 mmol), and the reaction mixture was stirred at rt for 3 h, diluted with TEA (0.1 mL), AcCN (0.5 mL) and water (0.5 mL), and purified by reverse-phase HPLC eluting with 40 to 90% AcCN in water (containing 0.1% TEA) to give the pivaloyloxymethyl ester of the title compound containing some impurities. Further purification by HPLC on a chiralpak AD column eluting with 35% isopropyl alcohol in heptane provided the pivaloyloxymethyl ester of the title compound. 1H NMR (500 MHz, CD$_3$OD): δ 8.62 (s, 2H), 8.22 (br s, 1H), 8.03 (br d, 1H), 8.00 (br d, 1H), 7.75 (t, 1H), 7.62 (d, 2H), 7.32 (d, 2H), 5.85 (d, 1H), 5.77 (d, 1H), 4.78 (dd, 1H), 3.80 (d, 1H), 3.50-3.40 (m, 2H), 3.30-3.22 (m, 2H), 3.10 (dd, 1H), 1.92 (m, 1H), 1.43 (m, 1H), 1.20 (s, 9H), 0.89 (s, 9H). LC-MS: calculated for C37H42Cl2N6O8S 800, observed m/e 801 (M+H)$^+$ (3.1 min).

1-(Ethoxycarbonyloxy)ethyl ester (R$^1$=—CH(CH$_3$)OC(O)OCH$_2$CH$_3$) This ester was prepared following the same procedure as described above for the pivaloylmethyl ester replacing chloromethyl pivalate with 1-chloroethyl ethyl carbonate. LC-MS: calculated for C36H40Cl2N6O9S 802, observed m/e 803 (M+H)$^+$ (3.2 min).

EXAMPLE 3

N-{N-[(3-Cyanobenzene)sulfonyl]-4(R)-azetidinyl-(L)-prolyl}-4-[(3',5'-dichloroisonicotinoyl)amino]-(L)-phenylalanine, Ethyl Ester

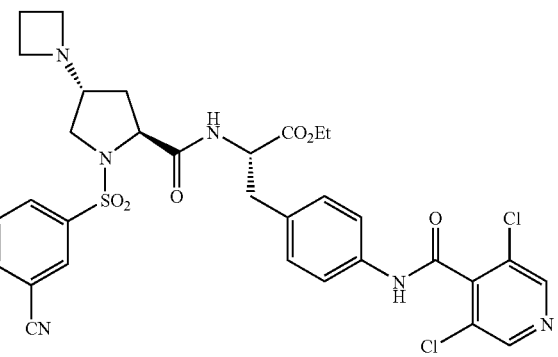

The title compound was prepared following procedures described for Example 1, Step A-D replacing cyclobutylamine at Step A with azetidine. $^1$H NMR (500 MHz, CD$_3$OD): δ 8.62 (s, 2H), 8.22 (br s, 1H), 8.03 (br d, 2H). 7.75 (t, 1H), 7.62 (d, 2H), 7.32 (d, 2H), 4.73 (dd, 1H), 4.24 (dd, 1H), 4.18 (q, 2H), 3.42 (dd, 1H), 3.23 (dd, 1H), 3.08 (d, 1H), 3.06 (dd, 1H), 2.97 (m, 2H), 2.88 (m, 2H), 2.82 (m, 1H), 1.85-1.75 (m, 3H), 1.74-1.68 (1H). LC-MS: calculated for C32H32Cl2N6O6S 698, observed m/e 699 (M+H)$^+$ (3.1 min).

EXAMPLE 4

(4R)-1-[(3-Cyanophenyl)sulfonyl]-4-(piperidinium-1-yl)-L-prolyl-4-[(3,5-dichloroisonicotinoyl)amino]-L-phenylalanine Trifluoroacetate

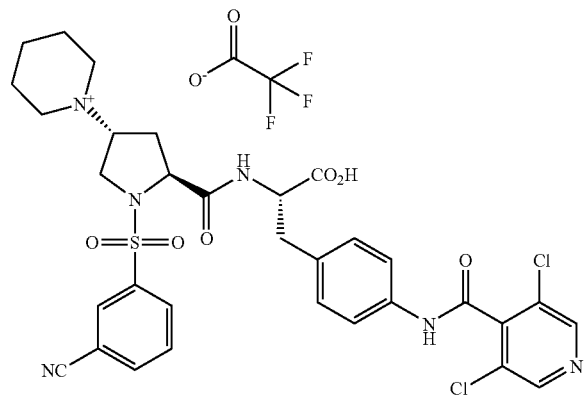

Step A: Compound of Reference Example 3 (3.0 g, 9.67 mmol) was dissolved in 100 mL CH$_2$Cl$_2$. N,N-Diisopropylethylamine (4.23 mL, 24.22 mmol) was added and the reaction mixture was cooled to −78° C. under N$_2$. Trifluoromethanesulfonic anhydride (2.28 mL, 13.55 mmol) was added dropwise to the solution over 10 minutes. The mixture was stirred for 1 hour at −78° C. and then slowly warmed to −30° C. over 30 minutes. Piperidine (1.91 mL, 19.31 mmol) was added dropwise over 5 minutes, and the solution was allowed to warm to room temperature and stirred overnight. 50 mL H$_2$O was added to the solution. The aqueous layer was extracted three times with CH$_2$Cl$_2$. The combined organic layers were dried over MgSO$_4$ and concentrated. The residue was purified by flash chromatography to give methyl (4R)-1-[(3-cyanophenyl)sulfonyl]-4-(piperidin-1-yl)prolinate (3.61 g, 99%) as a orange oil, which was dissolved in 15 mL acetonitrile and 5 mL H$_2$O. Lithium hydroxide (1.00 g, 23.84 mmol) was added, and the reaction mixture was stirred at room temperature for 1 hour. LCMS showed no starting material remained, so the reaction mixture was neutralized with 23.84 mL 1N HCl (23.84 mmol). The solution was frozen in an acetone-dry ice bath and lyopholized for 16 hours to give crude (4R)-1-[(3-cyanophenyl)sulfonyl]-4-(piperidin-1-yl)proline, which was used directly in the next reaction without further purification. MS (ESI) calculated for C17H21N3O4S 363.4, observed m/e 364.2 (MH$^+$).

Step B: The compound of Step A (9.56 mmol) was suspended in 25 mL DMF. (2S)-3-{4-[(3,5-dichloroisonicotinoyl)-amino]phenyl}-1-ethoxy-1-oxopropan-2-aminium chloride (3.99 g, 9.53 mmol), HATU (3.99 g, 10.49 mmol), and N-methylmorpholine (2.62 mL, 23.83 mmol) were added, and the reaction mixture was stirred for 24 hours at room temperature. The suspension was added dropwise to 100 mL H$_2$O with vigourous stirring. The precipitate was filtered immediately and washed three times with H$_2$O. The pale yellow powder was dried under vacuum and then purified by preparative reverse-phase HPLC to give ethyl (4R)-1-[(3-cyanophenyl)sulfonyl]-4-(piperidinium-1-yl)-L-prolyl-4-[(3,5-dichloroisonicotinoyl)amino]-L-phenylalaninate trifluoroacetate (4.42 g, 55%) as a white fluffy solid. $^1$H-NMR (MeOD, 500 MHz) δ 8.63 (s, 2H), 8.49 (d, 1H), 8.15 (s, 1H), 8.04-8.01 (m, 1H), 7.91-7.87 (m, 1H), 7.71 (t, 1H), 7.64 (d, 2H), 7.34 (d, 2H), 4.63-4.57 (m, 2H), 4.18 (q, 2H), 3.96-3.93 (m, 2H), 3.49-3.44 (m, 3H), 3.25-3.20 (m, 1H), 3.06-2.97 (m, 3H), 2.40-2.37 (m, 1H), 2.20-2.16 (m, 1H), 1.98-1.93 (m, 2H), 1.80-1.78 (m, 1H), 1.70-1.66 (m, 2H), 1.54-1.50 (m, 1H), 1.25 (t, 3H). MS (ESI) calculated for C34H36Cl2N6O6S 727.7, observed m/e 727.2 (M$^+$).

Step C: The compound of Step B (0.100 g, 0.14 mmol) was dissolved in 1.5 mL acetonitrile and 0.5 mL H$_2$O. Lithium hydroxide (0.014 g, 0.33 mmol) was added, and the reaction mixture was stirred at room temperature for 1 hour. LCMS showed no starting material remained, so the reaction mixture was neutralized with trifluoroacetic acid (0.03 mL, 0.33 mmol). The solution purified by preparative reverse-phase HPLC to give the title compound (0.043 g, 45%) as a fluffy white solid. $^1$H-NMR (MeOD, 500 MHz) δ 8.63 (s, 2H), 8.45 (d, 1H), 8.13 (s, 1H), 8.01 (d, 1H), 7.82 (d, 1H), 7.69-7.61 (m, 3H), 7.36 (d, 2H), 4.65-4.57 (m, 2H), 3.98-3.88 (m, 3H), 3.50-3.44 (m, 3H), 3.31-3.25 (m, 1H), 3.04-2.98 (m, 2H), 2.47-2.41 (m, 1H), 2.23-2.15 (m, 1H), 2.12-1.44 (m, 7H). MS (ESI) calculated for C$_{32}$H$_{32}$Cl$_2$N$_6$O$_6$S 699.6, observed n/e 699.1 (M$^+$).

EXAMPLE 4A

Ethyl(4R)-1-[(3-Cyanophenyl)sulfonyl]-4-(piperidinium-1-yl)-L-prolyl-4-[(3,5-dichloroisonicotinoyl)-amino]-L-phenylalaninate, and HCl and methanesulfonic acid salts The pale yellow crude powder of Example 4, Step B was purified by normal phase silica chromatography eluting with EtOAc (1% NH$_4$OH), followed by EtOAc (1% NH$_4$OH)/MeOH=99/1 to afford the compound free base as a white solid.

The title compound free base (200 mg, 0.28 mmol) was dissolved in EtOAc. Hydrochloric acid (4N in dioxane, 100 μL) was added dropwise and stirred at room temperature for 30 min. The precipitate obtained was filtered, washed with diethyl ether (3×) and dried under high vacuum to give the title compound HCl salt as a white solid.

The title compound free base (5.7 g, 7.8 mmol) was dissolved in EtOH (200 mL). Methanesulfonic acid (570 μL) was added dropwise and diethyl ether (200 mL) was added. The reaction mixture was stirred at room temperature for 4 hours. The precipitate obtained was filtered, washed with diethyl ether (3×) and dried under high vacuum to give the title compound methanesulfonic acid salt as a white solid.

The following compounds, as the trifluoroacetic acid salt, were prepared using the procedure described in Example 4:

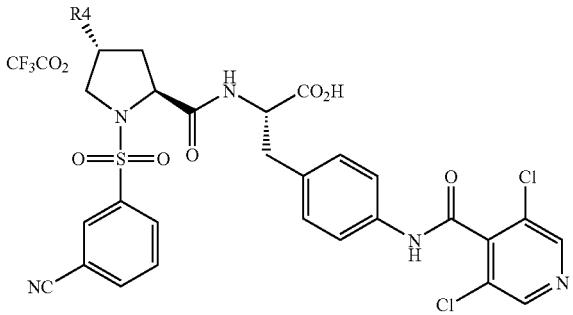

Example 5: R⁴ = 2-methylpiperidinium-1-yl
Ethyl ester: 1H-NMR (MeOD, 500 MHz) δ 8.63 (s, 3H), 8.21-8.09 (m, 1H), 8.05-8.01 (m, 1H), 7.97-7.88 (m, 1H), 7.77-7.69 (m, 1H), 7.61 (d, 2H), 7.34 (d, 2H), 4.63 (d, 1H), 4.64-4.51 (m, 1H), 4.19-4.14 (m, 2H), 3.99-3.78 (m, 1H), 3.80-3.67 (m, 1H), 3.53-3.38 (m, 1H), 3.29-3.19 (m, 2H), 3.09-3.00 (m, 1H), 2.37-2.32 (m, 1H), 2.26-2.10 (m, 1H), 2.04-1.79 (m, 3H), 1.78-1.55 (m, 3H), 1.42-1.30 (m, 3H), 1.29-1.22 (m, 3H). MS (ESI) calculated for $C_{35}H_{38}Cl_2N_6O_6S$ 741.7, observed m/e 741.2 (M+).
Acid: ¹H-NMR (MeOD, 500 MHz) δ 8.63 (s, 2H), 8.18-8.12 (m, 1H), 8.04-7.99 (m, 1H), 7.93-7.78 (m, 1H), 7.74-7.65 (m, 3H), 7.37 (d, 2H), 4.68-4.53 (m, 2H), 3.99-3.88 (m, 2H), 3.78-3.67 (m, 1H), 3.54-3.38 (m, 2H), 3.31-3.29 (m, 1H), 3.28-3.14 (m, 2H), 3.09-2.99 (m, 1H), 2.51-2.38 (m, 1H), 2.04-1.56 (m, 7H), 1.42-1.30 (m, 3H). MS (ESI) calculated for $C_{33}H_{34}Cl_2N_6O_6S$ 713.6, observed m/e 713.2 (M⁺).
Example 6: R⁴ = 3-methylpiperidinium-1-yl
Ethyl ester. ¹H-NMR (MeOD, 500 MHz) δ 8.63 (s, 2H), 8.59-8.54 (m, 1H), 8.15 (d, 1H), 8.02 (d, 1H), 7.87 (t, 1H), 7.70 (dt, 1H), 7.65 (d, 2H), 7.34 (d, 2H), 4.64-4.56 (m, 2H), 4.18 (q, 2H), 3.97-3.91 (m, 2H), 3.55-3.43 (m, 2H), 3.42-3.35 (m, 1H), 3.27-3.20 (m, 1H), 3.08-3.00 (m, 1H), 2.97-2.83 (m, 1H), 2.71-2.58 (m, 1H), 2.49-2.39 (m, 1H), 2.31-2.20 (m, 1H), 2.01-1.92 (m, 1H), 1.89-1.80 (m, 1H), 1.78-1.68 (m, 1H), 1.25 (t, 3H), 1.22-1.13 (m, 1H), 0.98 (d, 3H). MS (ESI) calculated for $C_{35}H_{38}Cl_2N_6O_6S$ 741.7, observed m/e 741.2 (M⁺).
Acid. ¹H-NMR (MeOD, 500 MHz) δ 8.62 (s, 2H), 8.48-8.43 (m, 1H), 8.13 (d, 1H), 8.00 (d, 1H), 7.82 (t, 1H), 7.69-7.63 (m, 3H), 7.36 (d, 2H), 4.65-4.55 (m, 2H), 3.95-3.88 (m, 2H), 3.53-3.41 (m, 2H), 3.40-3.33 (m, 1H), 3.30-3.28 (m, 1H), 3.05-2.98 (m, 1H), 2.97-2.79 (m, 1H), 2.73-2.59 (m, 1H), 2.54-2.43 (m, 1H), 2.31-2.21 (m, 1H), 2.02-1.92 (m, 1H), 1.89-1.80 (m, 2H), 1.79-1.68 (m, 1H), 1.28-1.17 (m, 1H), 0.98 (d, 3H). MS (ESI) calculated for $C_{33}H_{34}Cl_2N_6O_6S$ 713.6, observed m/e 713.2 (M⁺).
Example 7: R⁴ = 4-methylpiperidinium-1-yl
Ethyl ester. ¹H-NMR (MeOD, 500 MHz) δ 8.63 (s, 2H), 8.56 (d, 1H), 8.15 (s, 1H), 8.01 (d, 1H), 7.87 (d, 1H), 7.69 (t, 1H), 7.65 (d, 2H), 7.34 (d, 2H), 4.62-4.57 (m, 2H), 4.17 (q, 2H), 3.96-3.90 (m, 2H), 3.54-3.43 (m, 3H), 3.23 (dd, 1H), 3.09-2.92 (m, 3H), 2.43-2.39 (m, 1H), 2.28-2.20 (m, 1H), 1.92 (d, 2H), 1.77-1.63 (m, 1H), 1.43-1.31 (m, 2H), 1.25 (t, 3H), 0.98 (d, 3H). MS (ESI) calculated for $C_{35}H_{38}Cl_2N_6O_6S$ 741.7, observed m/e 743.2
Acid. ¹H-NMR (MeOD, 500 MHz) δ 8.63 (s, 2H), 8.45 (d, 1H), 8.13 (s, 1H), 8.00 (d, 1H), 7.83 (d, 1H), 7.69-7.63 (m, 3H), 7.36 (d, 2H), 4.64-4.56 (m, 2H), 3.93-3.88 (m, 2H), 3.50-3.43 (m, 3H), 3.40-3.25 (m, 1H), 3.09-2.93 (m, 3H), 2.46-2.41 (m, 1H), 2.24-2.17 (m, 1H), 1.92 (d, 2H), 1.79-1.63 (m, 1H), 1.45-1.30 (m, 2H), 0.98 (d, 3H). MS (ESI) calculated for $C_{33}H_{34}Cl_2N_6O_6S$ 713.6, observed m/e 713.1 (M⁺).
Example 8: R⁴ = 3,5-dimethylpiperidinium-1-yl
Ethyl ester. ¹H-NMR (MeOD, 500 MHz) δ 8.63 (s, 2H), 8.58 (d, 1H), 8.15 (s, 1H), 8.02 (d, 1H), 7.87 (d, 1H), 7.71 (t, 1H), 7.66 (d, 2H), 7.35 (d, 2H), 4.64-4.53 (m, 2H), 4.19 (q, 2H), 4.03-3.92 (m, 2H), 3.56-3.50 (m, 1H), 3.43-3.35 (m, 2H), 3.28-3.19 (m, 2H), 3.07-3.00 (m, 1H), 2.62-2.51 (m, 2H), 2.49-2.42 (m, 1H), 2.32-2.22 (m, 1H), 1.91-1.80 (m, 3H), 1.25 (t, 3H), 0.98 (d, 6H), 0.86 (q, 1H). MS (ESI) calculated for $C_{36}H_{40}Cl_2N_6O_6S$ 755.7, observed m/e 755.4 (M⁺).
Acid. ¹H-NMR (MeOD, 500 MHz) δ 8.62 (s, 2H), 8.47 (d, 1H), 8.13 (s, 1H), 8.00 (d, 1H), 7.82 (d, 1H), 7.69-7.63 (m, 3H), 7.37 (d, 2H), 4.64 (d, 1H), 4.61-4.56 (m, 1H), 4.02-3.91 (m, 2H), 3.51 (t, 1H), 3.41-3.34 (m, 2H), 3.31-3.27 (m, 1H), 3.06-2.99 (m, 1H), 2.62-2.48 (m, 3H), 2.29-2.21 (m, 1H), 1.92-1.81 (m, 3H), 0.98 (d, 6H), 0.86 (q, 1H). MS (ESI) calculated for $C_{34}H_{36}Cl_2N_6O_6S$ 727.6, observed m/e 727.2 (M⁺).
Example 9. R⁴ = 3,3-dimethylpiperidinium-1-yl
Ethyl ester. ¹H-NMR (MeOD, 500 MHz) δ 8.63 (s, 2H), 8.55-8.51 (m, 2H), 8.13 (d, 1H), 8.02 (t, 1H), 7.89-7.83 (m, 1H), 7.73-7.62 (m, 3H), 7.34 (d, 2H), 4.64-4.60 (m, 1H), 4.58-4.55 (m, 1H), 4.18 (q, 2H), 3.99-3.91 (m, 2H), 3.54-3.44 (m, 2H), 3.25-3.19 (m, 1H), 3.16 (d, 1H), 3.04-3.00 (m, 1H), 2.97-2.79 (m, 2H), 2.53-2.21 (m, 2H), 1.89-1.82 (m, 2H), 1.58-1.53 (m, 1H), 1.48-1.41 (m, 1H), 1.24 (t, 3H), 1.09 (d, 3H), 1.03 (s, 3H). MS (ESI) calculated for $C_{36}H_{40}Cl_2N_6O_6S$ 755.7, observed m/e 757.1 (MH⁺).
Acid. ¹H-NMR (MeOD, 500 MHz) δ 8.62 (s, 2H), 8.48 (d, 1H), 8.12 (s, 1H), 8.00 (d, 1H), 7.83-7.73 (m, 1H), 7.69-7.64 (m, 3H), 7.37 (d, 2H), 4.64 (d, 1H), 4.60-4.55 (m, 1H), 3.99-3.87 (m, 2H), 3.53-3.41 (m, 2H), 3.31-3.25 (m, 1H), 3.19-3.11 (m, 1H), 3.04-2.97 (m, 1H), 2.96-2.81 (m, 2H), 2.57-2.21 (m, 2H), 1.87-1.82 (m, 2H), 1.64-1.38 (m, 2H), 1.05 (s, 6H). MS (ESI) calculated for $C_{34}H_{36}Cl_2N_6O_6S$ 727.6, observed m/e 727.2 (M⁺).
Example 10: R⁴ = 4,4-dimethylpiperidinium-1-yl
Ethyl ester. ¹H-NMR (MeOD, 500 MHz) δ 8.63 (s, 2H), 8.58 (d, 1H), 8.15 (s, 1H), 8.01 (d, 1H), 7.87 (d, 1H), 7.69 (t, 1H), 7.65 (d, 2H), 7.34 (d, 2H), 4.64-4.57 (m, 2H), 4.18 (q, 2H), 4.10-4.03 (m, 1H), 3.94 (t, 1H), 3.49 (t, 1H), 3.42-3.33 (m, 2H), 3.27-3.20 (m, 1H), 3.19-3.09 (m, 2H), 3.08-3.01 (m, 1H), 2.45-2.40 (m, 1H), 2.30-2.21 (m, 1H), 1.69-1.62 (m, 4H), 1.24 (t, 3H), 1.04 (br s, 6H). MS (ESI) calculated for $C_{36}H_{40}Cl_2N_6O_6S$ 755.7, observed m/e 757.1 (MH⁺).

-continued

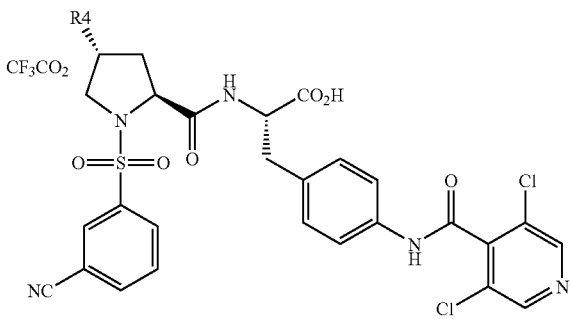

Acid. $^1$H-NMR (MeOD, 500 MHz) δ 8.62 (s, 2H), 8.47 (d, 1H), 8.13 (s, 1H), 8.01 (d, 1H), 7.83 (d, 1H), 7.69-7.63 (m, 3H), 7.37 (d, 2H), 4.64-4.57 (m, 2H), 4.07-4.02 (m, 1H), 3.93 (t, 1H), 3.49 (t, 1H), 3.41-3.31 (m, 2H), 3.30-3.25 (m, 1H), 3.24-3.09 (m, 2H), 3.05-2.98 (m, 1H), 2.48-2.42 (m, 1H), 2.29-2.19 (m, 1H), 1.70-1.59 (m, 4H), 1.03 (s, 6H). MS (ESI) calculated for $C_{34}H_{36}Cl_2N_6O_6S$ 727.6, observed m/e 727.2 (M$^+$).

Example 11. $R^4$ = octahydroquinolinium-1(2H)-yl
$^1$H-NMR (MeOD, 500 MHz) δ 8.65-8.61 (m, 2H), 8.59-8.52 (m, 1H), 8.23-8.18 (m, 1H), 8.08-8.01 (m, 1H), 8.01-7.89 (m, 1H), 7.78-7.68 (m, 1H), 7.67-7.57 (m, 2H), 7.38-7.23 (m, 2H), 4.71-4.50 (m, 2H), 4.24-4.13 (m, 2H), 4.06-3.92 (m, 2H), 3.59-3.48 (m, 1H), 3.45-3.39 (m, 1H), 3.29-3.14 (m, 3H), 3.12-3.01 (m, 2H), 2.47-2.30 (m, 1H), 2.22-2.12 (m, 1H), 2.11-2.02 (m, 1H), 2.01-1.58 (m, 8H), 1.52-1.32 (m, 4H), 1.30-1.21 (m, 3H). MS (ESI) calculated for $C_{38}H_{42}Cl_2N_6O_6S$ 781.7, observed m/e 781.4 (M$^+$).
Acid. $^1$H-NMR (MeOD, 500 MHz) δ 8.64-8.60 (m, 2H), 8.52-8.40 (m, 1H), 8.22-8.16 (m, 1H), 8.05-8.00 (m, 1H), 7.99-7.86 (m, 1H), 7.75-7.63 (m, 3H), 7.41-7.35 (m, 2H), 4.67-4.49 (m, 2H), 4.02-3.90 (m, 2H), 3.58-3.47 (m, 1H), 3.46-3.38 (m, 1H), 3.32-3.27 (m, 1H), 3.22-3.14 (m, 2H), 3.12-2.97 (m, 2H), 2.50-2.34 (m, 1H), 2.24-2.03 (m, 2H), 2.02-1.88 (m, 4H), 1.87-1.78 (m, 1H), 1.77-1.61 (m, 3H), 1.54-1.33 (m, 4H). MS (ESI) calculated for $C_{36}H_{39}Cl_2N_6O_6S$ 753.7, observed m/e 753.3 (M$^+$).
Example 12. $R^4$ = octahydroisoquinolinium-2(1H)-yl
Ethyl ester. $^1$H-NMR (MeOD, 500 MHz) δ 8.63 (s, 2H), 8.61-8.54 (m, 1H), 8.16-8.13 (m, 1H), 8.03-8.00 (m, 1H), 7.88-7.83 (m, 1H), 7.73-7.67 (m, 1H), 7.63 (d, 2H), 7.34 (d, 2H), 4.66-4.54 (m, 2H), 4.19 (q, 2H), 4.16-3.91 (m, 2H), 3.57-3.46 (m, 1H), 3.32-3.03 (m, 5H), 2.54-2.07 (m, 3H), 2.06-1.70 (m, 5H), 1.69-1.58 (m, 3H), 1.55-1.30 (m, 5H), 1.25 (t, 3H). MS (ESI) calculated for $C_{38}H_{42}Cl_2N_6O_6S$ 781.7, observed m/e 781.4 (M$^+$).
Acid. $^1$H-NMR (MeOD, 500 MHz) δ 8.63 (s, 2H), 8.49-8.44 (m, 1H), 8.14-8.12 (m, 1H), 8.02-7.99 (m, 1H), 7.84-7.79 (m, 1H), 7.69-7.53 (m, 3H), 7.37 (d, 2H), 4.67-4.56 (m, 2H), 4.11-3.90 (m, 2H), 3.56-3.46 (m, 1H), 3.34-3.31 (m, 2H), 3.22-3.00 (m, 3H), 2.60-2.49 (m, 1H), 2.29-2.16 (m, 1H), 2.15-1.83 (m, 4H), 1.82-1.70 (m, 3H), 1.69-1.58 (m, 3H), 1.57-1.44 (m, 1H), 1.43-1.22 (m, 4H). MS (ESI) calculated for $C_{36}H_{39}Cl_2N_6O_6S$ 753.7, observed m/e 753.3 (M$^+$).
Example 13. $R^4$ = 2-azonizbicyclo[2.2.2]-oct-2-yl
Methyl ester. $^1$H-NMR (Acetone-d6, 500 MHz) δ 9.92 (s, 1H), 8.67 (s, 2H), 8.23 (s, 1H), 8.11-8.06 (m, 2H), 7.83-7.75 (m, 4H), 7.53-7.45 (d, 2H), 4.78-4.76 (m, 1H), 4.62-4.60 (m, 1H), 4.22-4.15 (m, 2H), 3.64-3.58 (m, 3H), 3.42-3.37 (m, 3H), 3.30 (s, 3H), 3.25-3.21 (dd, 1H), 2.36-2.32 (m, 1H), 2.15-2.11 (m, 2H), 1.97 (m, 1H), 1.86-1.70 (m, 6H). MS (ESI) calculated for $C_{35}H_{36}Cl_2N_6O_6S$ 739.7, observed m/e 739.7 (M+).
Acid. $^1$H-NMR (Acetone-d6, 500 MHz) δ 9.93 (s, 1H), 8.66 (s, 2H), 8.23 (s, 1H), 8.11-8.06 (m, 2H), 7.80-7.71 (m, 4H), 7.41-7.39 (d, 2H), 4.78-4.76 (m, 1H), 4.62-4.60 (m, 1H), 4.22-4.20 (m, 1H), 4.03-4.00 (m, 1H), 3.64-3.58 (m, 3H), 3.40-3.38 (m, 2H), 3.27-3.24 (dd, 1H), 3.16-3.12 (dd, 1H), 2.36-2.32 (m, 1H), 2.18-2.14 (m, 2H), 1.97 (m, 1H), 1.86-1.70 (m, 5H), 1.29-1.31 (m, 1H). MS (ESI) calculated for $C_{34}H_{34}Cl_2N_6O_6S$ 725.7, observed m/e 725.7 (M$^+$).

What is claimed is:
1. A compound of formula I:

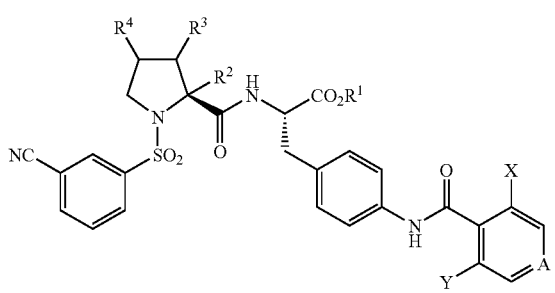

I or a pharmaceutically acceptable salt thereof, wherein:
A is N or N$^+$—O$^-$;
X and Y are independently selected from halogen, $C_{1-3}$alkyl, and $C_{1-3}$alkoxy;
$R^1$ is selected from (1) hydrogen, (2) $C_{1-10}$alkyl, (3) —($C_{1-10}$alkyl)-aryl, (4) —($C_{1-10}$alkyl)-O—$C_{1-10}$alkyl, (5) —($C_{1-10}$alkyl)-OC(O)—$C_{1-10}$alkyl, (6) —($C_{1-10}$alkyl)-OC(O)-aryl, (7) —($C_{1-10}$alkyl)-OC(O)O—$C_{1-10}$alkyl and (8) —($C_{1-10}$alkyl)N$^+$($C_{1-3}$alkyl)$_3$; wherein alkyl is optionally substituted with one to three substituents independently selected from R$^a$, and aryl is optionally substituted with one to three substituents independently selected from R$^b$;
$R^2$ is hydrogen or methyl;
$R^3$ and $R^4$ are independently selected from (1) hydrogen, (2) —NR$^d$R$^e$, (3) —NR$^d$S(O)$_m$R$^e$, (4) —NR$^d$C(O)R$^e$, (5) —NR$^d$C(O)OR$^e$, and (6) —NR$^d$C(O)NR$^d$R$^e$, with the proviso that R$^3$ and R$^4$ are not both hydrogen;

$R^a$ is selected from (1) —$OR^d$, (2) —$NR^dS(O)_mR^e$, (3) —$NO_2$, (4) halogen, (5) —$S(O)_mR^d$, (6) —$SR^d$, (7) —$S(O)_2R^d$, (8) —$S(O)_mNR^dR^e$, (9) —$NR^dR^e$, (10) —$O(CR^fR^g)_nNR^dR^e$, (11) —$C(O)R^d$, (12) —$CO_2R^d$, (13) —$CO_2(CR^fR^g)_nCONR^dR^e$, (14) —$OC(O)R^d$, (15) —CN, (16) —$C(O)NR^dR^e$, (17) —$NR^dC(O)R^e$, (18) —$OC(O)NR^dR^e$, (19) —$NR^dC(O)OR^e$, (20) —$NR^dC(O)NR^dR^e$, (21) —$CR^d(N—OR^e)$, (22) $CF_3$, (23) —$OCF_3$, (24) $C_{3-8}$cycloalkyl, and (25) heterocyclyl; wherein cycloalkyl and heterocyclyl are optionally substituted with one to three groups independently selected from $R^c$;

$R^b$ is selected from (1) a group selected from $R^a$, (2) $C_{1-10}$alkyl, (3) $C_{2-10}$ alkenyl (4) $C_{2-10}$ alkynyl, (5) aryl, and (6) —($C_{1-10}$alkyl)-aryl, wherein alkyl, alkenyl, alkynyl, and aryl are optionally substituted with one to three substituents selected from a group independently selected from $R^c$;

$R^c$ is (1) halogen, (2) amino, (3) carboxy, (4) $C_{1-4}$alkyl, (5) $C_{1-4}$alkoxy, (6) aryl, (7) —($C_{1-4}$alkyl)-aryl, (8) hydroxy, (9) $CF_3$, (10) $OC(O)C_{1-4}$alkyl, (11) $OC(O)NR^fR^g$, or (12) aryloxy;

$R^d$ and $R^e$ are independently selected from hydrogen, $C_{1-10}$alkyl, $C_{2-10}$alkenyl, $C_{2-10}$alkynyl, Cy and —($C_{1-10}$alkyl)-Cy, wherein alkyl, alkenyl, alkynyl and Cy are optionally substituted with one to four substituents independently selected from $R^c$; or $R^d$ and $R^e$ together with the atom(s) to which they are attached form a heterocyclic ring of 4 to 7 members containing 0-2 additional heteroatoms independently selected from O, S and N—$R^h$, and wherein said heterocyclic ring is optionally fused with a $C_{3-8}$ carbocyclic ring or is optional substituted with 1 to 4 groups independently selected from $C_{1-10}$alkyl;

$R^f$ and $R^g$ are independently selected from hydrogen, $C_{1-10}$alkyl, Cy and —($C_{1-10}$alkyl)-Cy; or $R^f$ and $R^g$ together with the carbon to which they are attached form a ring of 5 to 7 members containing 0-2 heteroatoms independently selected from oxygen, sulfur and nitrogen;

$R^h$ is selected from $R^f$ and —$C(O)R^f$;

Cy is selected from cycloalkyl, heterocyclyl, aryl, and heteroaryl; and m is 1 or 2.

2. A compound of claim 1 wherein one of X and Y is halogen and the other is selected from halogen, $C_{1-3}$alkyl and $C_{1-3}$alkoxy.

3. A compound of claim 1 wherein $R^1$ is hydrogen, $C_{1-4}$alkyl, —($C_{1-4}$alkyl)OC(O)—$C_{1-4}$alkyl, or —($C_{1-4}$alkyl)OC(O)—$C_{1-4}$alkyl.

4. A compound of claim 1 wherein $R^3$ is hydrogen, and $R^4$ is $NR^dR^e$.

5. A compound of claim 1 wherein $R^3$ is $NR^dR^e$ and $R^4$ is hydrogen.

6. A compound of claim 1 having the formula Ia:

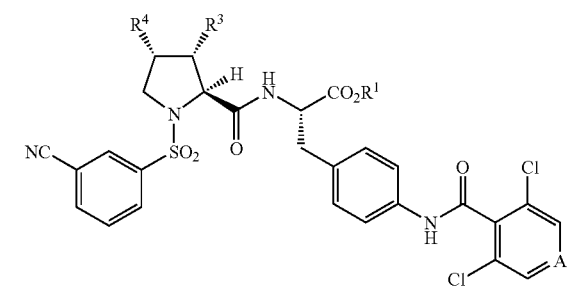

Ia or a pharmaceutically acceptable salt thereof, wherein
A is N or $N^+O^-$;
$R^1$ is selected from hydrogen, $C_{1-10}$alkyl, —($C_{1-4}$alkyl)-aryl, —($C_{1-4}$alkyl)-O—$C_{1-4}$alkyl, and —($C_{1-4}$alkyl)-OC(O)—$C_{1-4}$alkyl;
one of $R^3$ and $R^4$ is $NR^dR^e$ and the other is hydrogen.

7. A compound of claim 6 wherein $R^d$ is hydrogen and $R^e$ is t-butyl or cyclobutyl.

8. A compound of claim 6 wherein $R^3$ is hydrogen, and $R^d$ and $R^e$ together with the nitrogen atom to which they are attached form a heterocyclic ring of 4 to 7 members containing no additional heteroatom and optionally substituted with 1 or 2 groups independently selected from $C_{1-4}$alkyl.

9. A pharmaceutical composition comprising a therapeutically effective amount of a compound of claim 1 or a pharmaceutically acceptable salt thereof and a pharmaceutically acceptable carrier.

* * * * *